US009352032B2

(12) United States Patent
Borca et al.

(10) Patent No.: US 9,352,032 B2
(45) Date of Patent: May 31, 2016

(54) LIVE ATTENUATED ANTIGENICALLY MARKED CLASSICAL SWINE FEVER VACCINE

(71) Applicants: The United States of America, as Represented by the Secretary of Agriculture, Washington, DC (US); The University of Connecticut, Storrs, CT (US)

(72) Inventors: Manuel V. Borca, Westbrook, CT (US); Guillermo R. Risatti, Westbrook, CT (US); Lauren G. Holinka-Patterson, Deep River, CT (US)

(73) Assignees: The United States of America as represented by The Secretary of Agriculture, Washington, DC (US); The University of Conneticut, Farmington, CT (US)

( * ) Notice: Subject to any disclaimer, the term of this patent is extended or adjusted under 35 U.S.C. 154(b) by 98 days.

(21) Appl. No.: 14/200,802

(22) Filed: Mar. 7, 2014

(65) Prior Publication Data

US 2015/0250866 A1 Sep. 10, 2015

(51) Int. Cl.
*C12N 7/00* (2006.01)
*A61K 39/12* (2006.01)
*G01N 33/569* (2006.01)

(52) U.S. Cl.
CPC . *A61K 39/12* (2013.01); *C12N 7/00* (2013.01); *G01N 33/56983* (2013.01); *C12N 2770/24321* (2013.01); *C12N 2770/24334* (2013.01); *C12N 2770/24351* (2013.01); *C12N 2770/24371* (2013.01); *G01N 2333/183* (2013.01)

(58) Field of Classification Search
None
See application file for complete search history.

(56) References Cited

U.S. PATENT DOCUMENTS 8,133,495 B2 3/2012 Borca et al.

OTHER PUBLICATIONS

Edwards, S. et al., The development of an international reference panel of monoclonal antibodies for the differentiation of hog cholera virus from other pestiviruses, Veterinary Microbiology, (1991), vol. 29, pp. 101-108, Elsevier Science Publishers, B.V., Amsterdam.
Holinka, L.G., et al., Development of a live attenuated antigenic marker classical swine fever vaccine, Virology, (2009), vol. 384, pp. 106-113, Elsevier Science Publishers, B.V., Amsterdam.
Risatti, G.R., et al., Mutation of El glycoprotein of classical swine fever virus affects viral virulence in swine, Virology, (2005), vol. 343, pp. 116-127, Elsevier Science Publishers, B.V., Amsterdam.
Risatti, G.R., et al., The E2 glycoprotein of classical swine fever virus is a virulence determinant in swine, Journal of Virology, (Mar. 2005), vol. 79, (6), pp. 3787-3796, American Society for Microbiology.
Risatti, G.R., et al., Identification of a novel virulence determinant within the E2 structural glycoprotein of classical swine fever virus, Virology, (2006), vol. 355, pp. 94-101, Elsevier Science Publishers, B.V., Amsterdam.

*Primary Examiner* — Michelle S Horning
(74) *Attorney, Agent, or Firm* — John D. Fado; Evelyn M. Rabin

(57) ABSTRACT

Controlling Classical Swine Fever Virus (CSFV) involves either prophylactic vaccination or non-vaccination and elimination of infected herds depending on the epidemiological situation. Marker vaccines allowing distinction between naturally infected from vaccinated swine could complement "stamping out" measures. Previously, we reported the development of FlagT4v, a double antigenic marker live attenuated CSFV strain. FlagT4v was later shown as not to be completely stable in terms of its attenuation when assessed in a reversion to virulence protocol. We have developed a modified version of the FlagT4v where changes in the codon usage of genomic areas encoding for Flag and T4 were introduced to rectify the reversion to the virulent genotype. The new virus, FlagT4-mFT-Gv, possesses the same amino acid sequence as FlagT4v except for one substitution, Asparagine is replaced by Glycine at position 852 of the CSFV polypeptide. FlagT4-mFT-Gv protected swine against challenge with Brescia virulent virus at 21 days post vaccination.

10 Claims, 3 Drawing Sheets
(3 of 3 Drawing Sheet(s) Filed in Color)

SEQUENCE LISTING

<160> NUMBER OF SEQ ID NOS: 19

<210> SEQ ID NO 1
<211> LENGTH: 12357
<212> TYPE: DNA
<213> ORGANISM: Classical Swine Fever Virus

<400> SEQUENCE: 1

```
gtatacgagg ttagttcatt ctcgtgtaca tgattggaca aatcaaaatc tcaatttggt      60
tcagggcctc cctccagcga cggccgagct gggctagcca tgcccacagt aggactagca     120
aacggaggga ctagccgtag tggcgagctc cctgggtggt ctaagtcctg agtacaggac     180
agtcgtcagt agttcgacgt gagcagaagc ccacctcgag atgctatgtg dacgagggca     240
tgcccaagac acaccttaac cctagcgggg gtcgttaggg tgaaatcaca ccatgtgatg     300
ggagtacgac ctgatagggt gctgcagagg cccactatta ggctagtata aaaatctctg     360
ctgtacatgg cacatggagt tgaatcattt tgaactttta tacaaaacaa acaaacaaaa     420
accaatggga gtggaggaac cggtatacga tgtaacgggg agaccattgt ttggagaccc     480
aagtgaggta cacccacaat caacattgaa gctaccacat gatagggga gaggcaacat     540 caaaacaaca ctgaagaacc tacctaggag aggtgactgc aggagtggca accacctagg     600
cccggttagt gggatatatg taaagcccgg ccctgtcttt tatcaggact catgggccc     660 agtctatcat agagcccctc tagagttttt tgacgaagca cagttttgtg aggtgaccaa     720
aaggataggt agggtgacag tagtgacgg aaagctttac catatatacg tgtgcatcga     780
tggttgcatc ctgctgaagc tagccaagag gggcgagcca agaaccctga agtggattag     840
aaatctcacc gactgtccat tgtgggttac cagttgttct gatgatggtg caagtgcaag     900
taaagagaag aaaccagata ggatcaacaa gggtaaatta agatagccc caaaagagca     960 tgagaaggac agcaggacta agccacctga tgctacgatt gtagtggaag gagtaaaata    1020
ccaggtcaaa aagaaaggta agttaagggg aaagaatacc caagacggcc tgtaccacaa    1080
caagaataaa ccaccagaat ctaggaagaa attagaaaaa gccctattgg catgggcagt    1140
gatagcaatt atgttatacc aacctgttgc agccgaaaat ataactcaat ggaacctgag    1200
tgacaacggt accaatggta tccagcacgc tatgtacctt agaggagtca gcagaagctt    1260
gcatgggatc tggccagaaa aaatatgcaa aggagtcccc acctacctgg ccacagacac    1320
ggaactgaga gaaatacagg gaatgatgga tgccagcgag gggacaaact atacgtgctg    1380
taagttacag agacatgaat ggaacaaaca tggatggtgt aactggtata acatagaccc    1440
ctggatacag ttgatgaata gaacccaagc aaacttggca gaaggccctc cgagcaagga    1500
gtgcgccgtg acttgcaggt acgataaaaa tgctgacatt aacgtggtca cccaggccag    1560
aaacaggcca accaccctaa ctggctgcaa gaaagggaaa attttttctt ttgcgggtac    1620
agttatagag ggcccatgta atttcaacgt ttctgttgag gatatcttat atgggatca    1680 tgagtgtggc agtctactcc aggatacggc tctataccta gtagatggaa tgaccaacac    1740
tatagagaga gccaggcagg gagccgcgag ggtgacatct tggctaggga ggcaactcag    1800
aactgccggg aagaggttgg agggcagaag caaaacctgg tttggtgcct atgccctatc    1860
accttattgt aatgtgacaa gcaaataggg gtacatatgt acactaaca actgtacccc    1920 ggcttgcctc cccaaaaata caagataat aggccccggt aaatttgaca ctaacgcgga    1980
agacggaaag attctccatg agatggggggg ccacctatca gaatttctgc tgctctctct    2040
ggtcgttctg tctgacttcg cccctgaaac agccagcgcg ttatacctca ttttgcacta    2100
```

```
cgtgatccct caatcccatg aagaacctga aggctgtgac acaaaccagc tgaatttaac    2160
agtggaactc aggactgaag acgtgatacc atcatcagtc tggaatgttg gcaaatatgt    2220
gtgtgttaga ccagactggt ggccatatga aaccaaggtg gctttgttat ttgaagaggc    2280
aggacaggtc gtaaagttag ccttgcgggc actgagggat ttaaccaggg tctggaatag    2340
cgcatcaacc acggcattcc tcatctgctt gataaaagta ttaagaggac aggtcgtgca    2400
aggtgtgata tggctgttac tggtaactgg ggcaccagtg agttgcaccc acttagccgc    2460
ggccgactat aaagacgatg atgacaaagg ggcacaaggc cggctagcct gcaaggaaga    2520
tcacaggtac gctatatcaa caaccaatga gatagggcta cttggggccg aaggtctcac    2580
taccacctgg aaagaataca accacaattt gcaactggat gatgggaccg tcaaggccat    2640
ctgcatggca ggttcccttta aagtcacagc acttaatgtg gttagtagga ggtatctggc    2700
atcattacat aaggacgctt tacccacttc cgtgacattc gagctcctgt tcgacgggac    2760
cagcccattg accgaggaaa tgggagatga cttcgggttc ggactgtgtc cgtatgatac    2820
gagccctgta gtcaagggaa agtacaacac aaccttgttg aatggtagtg cattctacct    2880
agtttgccca ataggggtgga cgggtgttat agagtgcacg agtttcggaa tggatactct    2940
gagaacagaa gtggtaaaga ccttcagaag agagaaaccc tttccgtaca aagggattg    3000 tgtgaccact acagtggaaa atgaagatct attctactgt aaatgggggg gcaattggac    3060
atgtgtgaaa ggtgaaccag tgacctacac ggggggggcca gtaaaacaat gcagatggtg    3120
tggcttcgac ttcaatgagc ctgacggact cccacactac cccataggta agtgcatttt    3180
ggcaaatgag acaggttaca gaatagtgga ttcaacggac tgtaacagag atggcgttgt    3240
aatcagcaca gaggggagtc atgagtgctt gattggtaac acaactgtca aggtgcatgc    3300
attagatgaa agactaggcc ctatgccatg caggcctaag gagatcgtct ctagtgcggg    3360
acctgtaagg aaaacttcct gtacattcaa ctacgcaaaa actctgagga acaggtatta    3420
tgagcccagg gacagctatt tccaacaata tatgctcaag ggcgagtatc agtactggtt    3480
tgatctggat gtgaccgacc gccactcaga ttacttcgca gaattcattg tcttggtggt    3540
ggtggcactg ttgggaggaa gatatgtcct gtggctaata gtgacctaca agttctaacc    3600
agaacaactc gccgctggtc tacagttagg ccagggtgag gtagtgttaa tagggaactt    3660
aatcacccac acagatattg aggttgtagt atatttctta ctgctctatt tggtcatgag    3720
agatgagcct ataaagaaat ggatactact gctgttccat gctatgacca acaatccagt    3780
taagaccata acagtggcac tgctcatggt tagcggggtt gccaagggtg aaagatagaa    3840
tggtggttgg cagcggctgc cggagaccaa ctttgatatc caactcgcgc tgacagttat    3900
agtagtcgct gtgatgttgc tggcaaagaa agatccgact accgtcccct tggttataac    3960
ggtggcaacc ctgagaacgg ctaagataac taatggactt agtacagatc tagccatagc    4020
tacagtgtca acagctttgc taacctggac ctacattagt gactattata aatacaagac    4080
cttgctacag taccttatta gcacagtgac aggtatcttc ttgataaggg tactgaaggg    4140
ggtaggtgag ttagatttac acacccccaac cttaccatct tacagacccc tcttcttcat    4200
cctcgtgtac ctcattttcca ctgcagtggt aacaagatgg aatctggaca tagccggatt    4260
gctgctgcag tgtgtcccaa ccctttttaat ggttttcacg atgtgggcag acatccttac    4320
cctgatcctc atactgccta cttacgagtt gacaaaacta tattacctca aggaagtgaa    4380
gattggggca gaaagggggct ggttgtggaa gaccaacttc aagagggtaa atgacatata    4440
```

```
cgaagttgac caagctggtg aggggggtgta ccttttccca tcaaaacaaa agacaggtac    4500
aataacaggt actatgttgc cattgatcaa agccatactc ataagttgca tcagcaataa    4560
gtggcaattt atatatctat tgtacttgat attcgaagtg tcttactacc ttcacaagaa    4620
gatcatagat gaaatagcag gagggaccaa cttcatctcg agacttgtag ccgctctgat    4680
tgaagccaat tgggccttttg acaacgaaga agttagaggt ttaaagaagt tcttcctgct    4740
gtctagtagg gttaaagaac tgatcatcaa acacaaagtg aggaatgaag tgatggtcca    4800
ctggtttggc gacgaagagg tctatgggat gccgaagctg gttggcttag tcaaggcagc    4860
aacactgagt aaaaataaac attgtatttt gtgcaccgtc tgtgaaaaca gagagtggag    4920
aggagaaacc tgcccaaaat gcggccgttt tgggccacca gtgacctgtg gcatgaccct    4980
agccgacttt gaagaaaaac actataagag gattttcttt agagaggatc aatcagaagg    5040
gccggttagg gaggagtatg cagggtatct gcaatataga gccagagggc aattattcct    5100
gaggaatctc ccggtgctag caacaaaagt caagatgctc ctggtcggaa atcttgggac    5160
ggaggtgggg gatttggaac accttggctg ggtgctcaga gggcctgccg tttgcaagaa    5220
ggttaccgaa catgagaaat gcaccacatc cataatggac aaattaactg ctttcttcgg    5280
tgttatgcca aggggcacca cacctagagc ccctgtgaga ttccccacct ctctcttaaa    5340
gataagaagg gggctggaaa ctggctgggc gtacacacac caaggtggca tcagttcagt    5400
ggaccatgtc acttgtggga aagacttact ggtatgtgac actatgggcc ggacaagggt    5460
tgtttgccaa tcaaataaca agatgacaga cgagtccgag tatggagtta aaactgactc    5520
cggatgcccg gagggagcta ggtgttacgt gttcaaccca gaggcagtta acatatccgg    5580
gactaaagga gccatggtcc acttacaaaa aactggagga gaattcacct gtgtgacagc    5640
atcagggact ccggccttct ttgatctcaa gaacctcaaa ggctggtcag gctgccgat    5700 atttgaggca tcaagtggaa gagtagtcgg cagggttaag gtcgggaaga atgaggactc    5760
taaaccaacc aagcttatga gtggaataca aacagtctcc aaaagtacca cagacttgac    5820
agaaatggta aagaaaataa caaccatgaa caggggagaa ttcagacaaa taacccttgc    5880
cacaggtgcc ggaaaaacca cggaactccc tagatcagtc atagaagaga taggaaggca    5940
taagagggtc ttggtcttga ttccctctgag ggcggcagca gagtcagtat accaatatat    6000
gagacaaaaa cacccaagca tagcattcaa cttgaggata ggggagatga aggaagggga    6060
catggccaca gggataacct atgcctcata tggttacttc tgtcagatgc acaacctaa    6120 gctgcgagcc gcgatggttg agtactcctt catattcctt gatgagtacc actgtgccac    6180 cccccgaacaa ttggctatca tgggaaagat ccacagattt tcagagaacc tgcgggtagt    6240
agccatgacc gcaacaccag caggcacggt aacaactaca gggcaaaaac acccctatag    6300
agaatacata gccccagaag tgatgaaggg ggaagactta ggttcagagt acttggacat    6360
agctggacta aagataccag tagaggagat gaagagtaac atgctggtct ttgtgcccac    6420
aaggaacatg gctgtagaga cggcaaagaa actgaaagct aagggttata actcaggcta    6480
ctattatagt ggagaggatc catctaacct gagggtggta acatcacagt ccccgtacgt    6540
ggtggtagca accaacgcaa tagaatcagg tgttactctc ccagacttgg atgtggtcgt    6600
cgacacaggg cttaagtgtg aaaagaggat acggctgtca cctaagatgc ccttcatagt    6660
gacgggcctg aagagaatgg ctgtcacgat tgggggaacaa gcccagagaa ggggagagt    6720 tgggagagtg aagcctggga gatactacag gagtcaagaa accccccgttg gttccaaaga    6780 ttaccattac gacctactgc aagcacagag gtacggtata agagatggga taaacatcac    6840
```

```
caaatctttt agagagatga attatgattg gagcctttat gaggaggata gtctgatgat   6900
tacacaattg gaaatcctca acaatctgtt gatatcagaa gagctaccaa tggcagtaaa   6960
aaatataatg gccaggactg accacccaga accaatccaa ctggcgtaca acagctacga   7020
aacgcaggtg ccagtgctat tcccaaaaat aaaaaatgga gaggtgactg acagttacga   7080
taactatacc ttcctcaacg caagaaagct gggggatgat gtacctccct acgtgtatgc   7140
cacagaggat gaggacttag cggtagagct gctgggctta gactggccgg accctgggaa   7200
ccaaggaacc gtggaggctg gtagagcact aaaacaagta gttggtctat caacagctga   7260
gaacgccctg ttagtagctt tattcggcta tgtaggatat caggcactct caaagaggca   7320
tataccagta gtcacagaca tatattcaat tgaagatcac aggttggaag acaccacaca   7380
cctacagtat gccccgaatg ctatcaagac ggaggggaag gagacagaat tgaaggagct   7440
agctcagggg gatgtgcaga gatgtatgga agctatgact aattatgcaa gagatggcat   7500
ccaattcatg aagtctcagg cactgaaagt gaaagaaacc cccacttaca aagagacaat   7560
ggacaccgtg gcggactatg taagaagtt catggaggca ctggcggaca gcaaagaaga   7620
catcataaaa tatgggttgt gggggacgca cacaacctta tataagagca tcggtgctag   7680
gcttgggaac gagactgcgt tcgctaccct ggtcgtgaaa tggctggcat ttgggggaga   7740
atcaatagca gaccatgtca aacaagcggc cacagacttg gtcgtttact atatcatcaa   7800
cagacctcag ttcccaggag acacggagac acaacaggaa ggaaggaaat tgtgtagccag  7860
cctactggtc tcagccctgg ctacttacac ttacaaaagc tggaattaca ataatctgtc   7920
caagatagtt gaaccggctt tggctactct gccctatgcc gccacagctc tcaagctatt   7980
cgccccact cgattggaga gcgttgtcat actgagtacc gcaatctaca aaacctacct   8040
atcaatcagg cgcggaaaaa gcgatggttt gctaggcaca ggggttagtg cggctatgga   8100
aatcatgtca caaacccag tatctgtggg tatagcggtc atgctagggg tggggccgt    8160
agcggcccac aatgcaatcg aagccagtga gcagaagaga acactactca tgaaagtttt   8220
tgtaaagaac ttcttggatc aggcagccac tgatgaatta gtcaaggaga gccctgagaa   8280
aataataatg gctttgtttg aagcagtgca gacagtcggc aaccctctta gactggtata   8340
ccacctttac ggagttttt acaaagggtg ggaggcaaaa gagttggccc aaaggacagc   8400
cggtaggaat cttttcactt tgataatgtt tgaggctgtg gaactactgg gagtagatag   8460
cgaaggaaag atccgccagc tatcaagcaa ttacatacta gagctcctgt ataagttccg   8520
tgacagtatc aagtccagcg tgaggcagat ggcaatcagc tgggcccctg ccccttttag  8580
ttgtgattgg acaccgacgg atgacagaat agggcttccc caagataatt tcctccgagt   8640
ggagacaaaa tgcccctgtg gttacaagat gaaagcagtt aagaattgtg ctggggagtt   8700
gagactctta gaagaggaag gctcatttct ctgcaggaat aaattcggga gaggttcacg   8760
gaactacagg gtgacaaaat actatgatga caatctatca gaaataaagc cagtgataag   8820
aatggaagga catgtggaac tctactacaa gggagccact attaaactgg atttcaacaa   8880
cagtaaaaca atattggcaa ccgataaatg ggaggtcgat cactccactc tggtcagggt   8940
gctcaagagg cacacagggg ctggatatcg tgggcatac ctgggtgaga accgaacca    9000
caaacatctg atagagaggg actgcgcaac catcaccaaa gataaggttt gttttctcaa   9060
gatgaagaga gggtgtgcat ttacttatga cttatccctt cacaacctta cccggctgat   9120
cgaattggta cacaagaata acttggaaga caaagagatt cctgccgtta cggtcacaac   9180
```

```
ctggctggct tacacatttg taaatgaaga tatagggacc ataaaaccag ccttcgggga    9240
gaaaataaca ccagagatgc aggaggagat aaccttgcag cctgctgtag tggtggatgc    9300
aactgacgtg accgtgaccg tggtagggga aacccctact atgactacag gggagacccc    9360
aacaacgttc accagctcag gtccagaccc gaaaggccaa caagttttaa aactgggagt    9420
aggtgaaggc caataccccg ggactaatcc acagagagca agcctgcacg aagccataca    9480
aagcgcagat gaaaggccct ctgtgttgat attggggtct gataaagcca cctctaatag    9540
agtgaaaact gtaaagaatg tgaaggtata cagaggcagg gacccactag aagtgagaga    9600
tatgatgagg aggggaaaga tcctagtcat agccctgtct agggttgata atgctctatt    9660
gaaatttgta gattacaaag gcacctttct aactagagag accctggagg cattaagttt    9720
gggtaggcca aaaagaaaaa acataaccaa ggcagaagca cagtggttgc tgcgcctcga    9780
agaccaaatg aagagctac ccgattggtt cgcagccggg aacccatttt ttttagaggc    9840
caatattaaa catgacaggt atcatctggt aggggatata gctactatca aagagaaagc    9900
caaacaattg ggggctacag actctacaaa gatatccaag gaggttggtg caaaagtata    9960
ttctatgaaa ttgagtaatt gggtgatgca agaagaaaac aaacagagca acttgacccc   10020
cttatttgaa gagctcctac agcagtgtcc acccggaggc caaaacaaaa ctgcacatat   10080
ggtctctgct taccaactag ctcaagggaa ctggatgcca accagctgcc atgtttttat   10140
ggggaccata tctgccagaa ggactaagac ccatccatat gaagcatatg tcaagttaag   10200
ggagttggta gaggaacaca agatgaaaac attgtgtccc ggatcaagtc tgcgtaagca   10260
caatgaatgg gtaattggca agatcaaata ccagggcaac ctgaggacca aacacatgtt   10320
gaaccccggc aaggtggcag agcaactgca cagagaagga cacagacaca atgtgtataa   10380
caagacaata ggctcagtga tgacagctac tggcatcagg ttggagaagt tgcccgtggt   10440
tagggcccag acagacacaa ccaacttcca ccaagcaata agggataaga tagacaagga   10500
agagaatcta cagaccccgg gtttacataa gaaactaatg gaagttttca atgcattgaa   10560
acgacccgag ttagagtcct cctatgacgc tgtggaatgg gaggaattgg agagaggaat   10620
aaacagaaag ggtgctgctg gtttctttga acgcaaaaac ataggggaga tattggattc   10680
agagaaaaat aaagtagaag agattattga caatctgaaa aagggtagaa atatcaaata   10740
ctatgaaacc gcaatcccaa aaaatgaaaa gagggatgtc aatgatgact ggaccgcagg   10800
tgactttgtg gacgagaaga acccagagt catacaatac cctgaagcaa aaacaaggct   10860
ggccatcacc aaggtgatgt ataagtgggg gaagcagaag ccagtagtca tacccgggta   10920
tgaagggaag acacctctgt tccaaatttt tgacaaagta agaaggaat gggatcaatt   10980
ccaaaatcca gtggcagtga gcttcgacac taaggcgtgg gacacccagg tgaccacaaa   11040
tgatctggag ctgataaagg acatacaaaa gtactacttc aagaagaaat ggcataaatt   11100
tattgacacc ctgactatgc atatgtcaga agtacccgta atcactgctg atgggggaggt   11160
gtatataagg aaagggcaaa gaggtagtgg acagcccgac acaagcgcag caacagcat   11220
gctaaatgtg ttaacaatgg tttatgcctt ctgcgaggcc acagggtac cctacaagag   11280
ttttgacagg tgtgcaaaaa ttcatgtgtg cggggacgat ggtttcctga tcacagagag   11340
agctctcggc gagaaattcg caagcaaggg agtccaaatc ctgtatgaag ctgggaagcc   11400
ccagaagatc actgaagggg acaaaatgaa agtggcctac caatttgatg atattgagtt   11460
ttgctcccat acaccaatac aagtaaggtg gtcagataac acttctagct acatgccagg   11520
gagaaataca accacaatcc tggctaaaat ggccacaagg ttagattcca gtggtgagag   11580
```

-continued

```
gggtaccata gcgtacgaga aagcagtagc attcagcttc ctgctaatgt attcctggaa   11640
cccactaatc agaaggattt gcttattggt actatcaact gaactgcaag tgaaaccagg   11700
gaagtcaacc acttactatt atgaagggga cccgatatct gcctacaagg aagtcatcgg   11760
ccacaatctt ttcgatctca agagaacaag cttcgagaag ctggccaagt taaatctcag   11820
catgtccgta ctcggggcct ggactagaca caccagcaaa agactactac aagactgtgt   11880
caatatgggt gttaaagagg gcaactggtt agtcaatgca gacagactgg tgagtagtaa   11940
gactggaaat aggtatgtac ctggagaagg ccacaccctg caagggagac attatgaaga   12000
actggtgttg gcaagaaaac agatcaacag cttccaaggg acagacaggt acaatctagg   12060
cccaatagtc aacatggtgt taaggaggct gagagtcatg atgatgaccc tgatagggag   12120
aggggtatga gtgcgggtga cccgcgatct ggacccgtca gtaggaccct attgtagata   12180
acactaattt tttatttatt tagatattac tatttattta tttatttatt tattgaatga   12240
gtaagaactg gtacaaacta cctcatgtta ccacactaca ctcattttaa cagcacttta   12300
gctggaagga aaattcctga cgtccacagt tggactaagg taatttccta acggccc     12357
```

<210> SEQ ID NO 2
<211> LENGTH: 3918
<212> TYPE: PRT
<213> ORGANISM: Classical Swine Fever Virus

<400> SEQUENCE: 2

```
Met Glu Leu Asn His Phe Glu Leu Leu Tyr Lys Thr Asn Lys Gln Lys
1               5                   10                  15

Pro Met Gly Val Glu Pro Val Tyr Asp Val Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Arg Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Ile Asp Gly Cys Ile Leu Leu Lys Leu Ala
    130                 135                 140

Lys Arg Gly Glu Pro Arg Thr Leu Lys Trp Ile Arg Asn Leu Thr Asp
145                 150                 155                 160

Cys Pro Leu Trp Val Thr Ser Cys Ser Asp Asp Gly Ala Ser Ala Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Lys Pro Pro Asp Ala Thr
        195                 200                 205

Ile Val Val Glu Gly Val Lys Tyr Gln Val Lys Lys Gly Lys Val
    210                 215                 220

Lys Gly Lys Asn Thr Gln Asp Gly Leu Tyr His Asn Lys Asn Lys Pro
225                 230                 235                 240
```

-continued

```
Pro Glu Ser Arg Lys Lys Leu Glu Lys Ala Leu Leu Ala Trp Ala Val
            245                 250                 255
Ile Ala Ile Met Leu Tyr Gln Pro Val Ala Ala Glu Asn Ile Thr Gln
                260                 265                 270
Trp Asn Leu Ser Asp Asn Gly Thr Asn Gly Ile Gln His Ala Met Tyr
            275                 280                 285
Leu Arg Gly Val Ser Arg Ser Leu His Gly Ile Trp Pro Glu Lys Ile
        290                 295                 300
Cys Lys Gly Val Pro Thr Tyr Leu Ala Thr Asp Thr Glu Leu Arg Glu
305                 310                 315                 320
Ile Gln Gly Met Met Asp Ala Ser Glu Gly Thr Asn Tyr Thr Cys Cys
                325                 330                 335
Lys Leu Gln Arg His Glu Trp Asn Lys His Gly Trp Cys Asn Trp Tyr
            340                 345                 350
Asn Ile Asp Pro Trp Ile Gln Leu Met Asn Arg Thr Gln Ala Asn Leu
        355                 360                 365
Ala Glu Gly Pro Pro Ser Lys Glu Cys Ala Val Thr Cys Arg Tyr Asp
    370                 375                 380
Lys Asn Ala Asp Ile Asn Val Val Thr Gln Ala Arg Asn Arg Pro Thr
385                 390                 395                 400
Thr Leu Thr Gly Cys Lys Lys Gly Lys Asn Phe Ser Phe Ala Gly Thr
                405                 410                 415
Val Ile Glu Gly Pro Cys Asn Phe Asn Val Ser Val Glu Asp Ile Leu
            420                 425                 430
Tyr Gly Asp His Glu Cys Gly Ser Leu Leu Gln Asp Thr Ala Leu Tyr
        435                 440                 445
Leu Val Asp Gly Met Thr Asn Thr Ile Glu Arg Ala Arg Gln Gly Ala
    450                 455                 460
Ala Arg Val Thr Ser Trp Leu Gly Arg Gln Leu Arg Thr Ala Gly Lys
465                 470                 475                 480
Arg Leu Glu Gly Arg Ser Lys Thr Trp Phe Gly Ala Tyr Ala Leu Ser
                485                 490                 495
Pro Tyr Cys Asn Val Thr Ser Lys Ile Gly Tyr Ile Trp Tyr Thr Asn
            500                 505                 510
Asn Cys Thr Pro Ala Cys Leu Pro Lys Asn Thr Lys Ile Ile Gly Pro
        515                 520                 525
Gly Lys Phe Asp Thr Asn Ala Glu Asp Gly Lys Ile Leu His Glu Met
    530                 535                 540
Gly Gly His Leu Ser Glu Phe Leu Leu Leu Ser Leu Val Leu Leu Ser
545                 550                 555                 560
Asp Phe Ala Pro Glu Thr Ala Ser Ala Leu Tyr Leu Ile Leu His Tyr
                565                 570                 575
Val Ile Pro Gln Ser His Glu Glu Pro Glu Gly Cys Asp Thr Asn Gln
            580                 585                 590
Leu Asn Leu Thr Val Glu Leu Arg Thr Glu Asp Val Ile Pro Ser Ser
        595                 600                 605
Val Trp Asn Val Gly Lys Tyr Val Cys Val Arg Pro Asp Trp Trp Pro
    610                 615                 620
Tyr Glu Thr Lys Val Ala Leu Leu Phe Glu Glu Ala Gly Gln Val Val
625                 630                 635                 640
Lys Leu Ala Leu Arg Ala Leu Arg Asp Leu Thr Arg Val Trp Asn Ser
                645                 650                 655
```

```
Ala Ser Thr Thr Ala Phe Leu Ile Cys Leu Ile Lys Val Leu Arg Gly
            660                 665                 670

Gln Val Val Gln Gly Val Ile Trp Leu Leu Leu Val Thr Gly Ala Pro
        675                 680                 685

Val Ser Cys Thr His Leu Ala Ala Ala Asp Tyr Lys Asp Asp Asp Asp
    690                 695                 700

Lys Gly Ala Gln Gly Arg Leu Ala Cys Lys Glu Asp His Arg Tyr Ala
705                 710                 715                 720

Ile Ser Thr Thr Asn Glu Ile Gly Leu Leu Gly Ala Glu Gly Leu Thr
                725                 730                 735

Thr Thr Trp Lys Glu Tyr Asn His Asn Leu Gln Leu Asp Asp Gly Thr
            740                 745                 750

Val Lys Ala Ile Cys Met Ala Gly Ser Phe Lys Val Thr Ala Leu Asn
        755                 760                 765

Val Val Ser Arg Arg Tyr Leu Ala Ser Leu His Lys Asp Ala Leu Pro
    770                 775                 780

Thr Ser Val Thr Phe Glu Leu Leu Phe Asp Gly Thr Ser Pro Leu Thr
785                 790                 795                 800

Glu Glu Met Gly Asp Asp Phe Gly Phe Gly Leu Cys Pro Tyr Asp Thr
                805                 810                 815

Ser Pro Val Val Lys Gly Lys Tyr Asn Thr Thr Leu Leu Asn Gly Ser
            820                 825                 830

Ala Phe Tyr Leu Val Cys Pro Ile Gly Trp Thr Gly Val Ile Glu Cys
        835                 840                 845

Thr Ser Phe Gly Met Asp Thr Leu Arg Thr Glu Val Val Lys Thr Phe
    850                 855                 860

Arg Arg Glu Lys Pro Phe Pro Tyr Arg Arg Asp Cys Val Thr Thr Thr
865                 870                 875                 880

Val Glu Asn Glu Asp Leu Phe Tyr Cys Lys Trp Gly Asn Trp Thr
                885                 890                 895

Cys Val Lys Gly Glu Pro Val Thr Tyr Thr Gly Pro Val Lys Gln
            900                 905                 910

Cys Arg Trp Cys Gly Phe Asp Phe Asn Glu Pro Asp Gly Leu Pro His
        915                 920                 925

Tyr Pro Ile Gly Lys Cys Ile Leu Ala Asn Glu Thr Gly Tyr Arg Ile
    930                 935                 940

Val Asp Ser Thr Asp Cys Asn Arg Asp Gly Val Val Ile Ser Thr Glu
945                 950                 955                 960

Gly Ser His Glu Cys Leu Ile Gly Asn Thr Thr Val Lys Val His Ala
                965                 970                 975

Leu Asp Glu Arg Leu Gly Pro Met Pro Cys Arg Pro Lys Glu Ile Val
            980                 985                 990

Ser Ser Ala Gly Pro Val Arg Lys Thr Ser Cys Thr Phe Asn Tyr Ala
        995                 1000                1005

Lys Thr Leu Arg Asn Arg Tyr Tyr Glu Pro Arg Asp Ser Tyr Phe
    1010                1015                1020

Gln Gln Tyr Met Leu Lys Gly Glu Tyr Gln Tyr Trp Phe Asp Leu
    1025                1030                1035

Asp Val Thr Asp Arg His Ser Asp Tyr Phe Ala Glu Phe Ile Val
    1040                1045                1050

Leu Val Val Val Ala Leu Leu Gly Gly Arg Tyr Val Leu Trp Leu
    1055                1060                1065

Ile Val Thr Tyr Ile Val Leu Thr Glu Gln Leu Ala Ala Gly Leu
```

-continued

```
            1070                1075                1080
Gln Leu Gly Gln Gly Glu Val Val Leu Ile Gly Asn Leu Ile Thr
            1085                1090                1095
His Thr Asp Ile Glu Val Val Tyr Phe Leu Leu Leu Tyr Leu
            1100                1105                1110
Val Met Arg Asp Glu Pro Ile Lys Lys Trp Ile Leu Leu Leu Phe
            1115                1120                1125
His Ala Met Thr Asn Asn Pro Val Lys Thr Ile Thr Val Ala Leu
            1130                1135                1140
Leu Met Val Ser Gly Val Ala Lys Gly Gly Lys Ile Asp Gly Gly
            1145                1150                1155
Trp Gln Arg Leu Pro Glu Thr Asn Phe Asp Ile Gln Leu Ala Leu
            1160                1165                1170
Thr Val Ile Val Val Ala Val Met Leu Leu Ala Lys Lys Asp Pro
            1175                1180                1185
Thr Thr Val Pro Leu Val Ile Thr Val Ala Thr Leu Arg Thr Ala
            1190                1195                1200
Lys Ile Thr Asn Gly Leu Ser Thr Asp Leu Ala Ile Ala Thr Val
            1205                1210                1215
Ser Thr Ala Leu Leu Thr Trp Thr Tyr Ile Ser Asp Tyr Tyr Lys
            1220                1225                1230
Tyr Lys Thr Leu Leu Gln Tyr Leu Ile Ser Thr Val Thr Gly Ile
            1235                1240                1245
Phe Leu Ile Arg Val Leu Lys Gly Val Gly Glu Leu Asp Leu His
            1250                1255                1260
Thr Pro Thr Leu Pro Ser Tyr Arg Pro Leu Phe Phe Ile Leu Val
            1265                1270                1275
Tyr Leu Ile Ser Thr Ala Val Val Thr Arg Trp Asn Leu Asp Ile
            1280                1285                1290
Ala Gly Leu Leu Leu Gln Cys Val Pro Thr Leu Leu Met Val Phe
            1295                1300                1305
Thr Met Trp Ala Asp Ile Leu Thr Leu Ile Leu Ile Leu Pro Thr
            1310                1315                1320
Tyr Glu Leu Thr Lys Leu Tyr Tyr Leu Lys Glu Val Lys Ile Gly
            1325                1330                1335
Ala Glu Arg Gly Trp Leu Trp Lys Thr Asn Phe Lys Arg Val Asn
            1340                1345                1350
Asp Ile Tyr Glu Val Asp Gln Ala Gly Glu Gly Val Tyr Leu Phe
            1355                1360                1365
Pro Ser Lys Gln Lys Thr Gly Thr Ile Thr Gly Thr Met Leu Pro
            1370                1375                1380
Leu Ile Lys Ala Ile Leu Ile Ser Cys Ile Ser Asn Lys Trp Gln
            1385                1390                1395
Phe Ile Tyr Leu Leu Tyr Leu Ile Phe Glu Val Ser Tyr Tyr Leu
            1400                1405                1410
His Lys Lys Ile Ile Asp Glu Ile Ala Gly Gly Thr Asn Phe Ile
            1415                1420                1425
Ser Arg Leu Val Ala Ala Leu Ile Glu Ala Asn Trp Ala Phe Asp
            1430                1435                1440
Asn Glu Glu Val Arg Gly Leu Lys Lys Phe Phe Leu Leu Ser Ser
            1445                1450                1455
Arg Val Lys Glu Leu Ile Ile Lys His Lys Val Arg Asn Glu Val
            1460                1465                1470
```

```
Met Val His Trp Phe Gly Asp Glu Glu Val Tyr Gly Met Pro Lys
    1475            1480            1485

Leu Val Gly Leu Val Lys Ala Ala Thr Leu Ser Lys Asn Lys His
    1490            1495            1500

Cys Ile Leu Cys Thr Val Cys Glu Asn Arg Glu Trp Arg Gly Glu
    1505            1510            1515

Thr Cys Pro Lys Cys Gly Arg Phe Gly Pro Pro Val Thr Cys Gly
    1520            1525            1530

Met Thr Leu Ala Asp Phe Glu Glu Lys His Tyr Lys Arg Ile Phe
    1535            1540            1545

Phe Arg Glu Asp Gln Ser Glu Gly Pro Val Arg Glu Glu Tyr Ala
    1550            1555            1560

Gly Tyr Leu Gln Tyr Arg Ala Arg Gly Gln Leu Phe Leu Arg Asn
    1565            1570            1575

Leu Pro Val Leu Ala Thr Lys Val Lys Met Leu Leu Val Gly Asn
    1580            1585            1590

Leu Gly Thr Glu Val Gly Asp Leu Glu His Leu Gly Trp Val Leu
    1595            1600            1605

Arg Gly Pro Ala Val Cys Lys Lys Val Thr Glu His Glu Lys Cys
    1610            1615            1620

Thr Thr Ser Ile Met Asp Lys Leu Thr Ala Phe Phe Gly Val Met
    1625            1630            1635

Pro Arg Gly Thr Thr Pro Arg Ala Pro Val Arg Phe Pro Thr Ser
    1640            1645            1650

Leu Leu Lys Ile Arg Arg Gly Leu Glu Thr Gly Trp Ala Tyr Thr
    1655            1660            1665

His Gln Gly Gly Ile Ser Ser Val Asp His Val Thr Cys Gly Lys
    1670            1675            1680

Asp Leu Leu Val Cys Asp Thr Met Gly Arg Thr Arg Val Val Cys
    1685            1690            1695

Gln Ser Asn Asn Lys Met Thr Asp Glu Ser Glu Tyr Gly Val Lys
    1700            1705            1710

Thr Asp Ser Gly Cys Pro Glu Gly Ala Arg Cys Tyr Val Phe Asn
    1715            1720            1725

Pro Glu Ala Val Asn Ile Ser Gly Thr Lys Gly Ala Met Val His
    1730            1735            1740

Leu Gln Lys Thr Gly Gly Glu Phe Thr Cys Val Thr Ala Ser Gly
    1745            1750            1755

Thr Pro Ala Phe Phe Asp Leu Lys Asn Leu Lys Gly Trp Ser Gly
    1760            1765            1770

Leu Pro Ile Phe Glu Ala Ser Ser Gly Arg Val Val Gly Arg Val
    1775            1780            1785

Lys Val Gly Lys Asn Glu Asp Ser Lys Pro Thr Lys Leu Met Ser
    1790            1795            1800

Gly Ile Gln Thr Val Ser Lys Ser Thr Thr Asp Leu Thr Glu Met
    1805            1810            1815

Val Lys Lys Ile Thr Thr Met Asn Arg Gly Glu Phe Arg Gln Ile
    1820            1825            1830

Thr Leu Ala Thr Gly Ala Gly Lys Thr Thr Glu Leu Pro Arg Ser
    1835            1840            1845

Val Ile Glu Glu Ile Gly Arg His Lys Arg Val Leu Val Leu Ile
    1850            1855            1860
```

```
Pro Leu Arg Ala Ala Ala Glu Ser Val Tyr Gln Tyr Met Arg Gln
    1865             1870             1875

Lys His Pro Ser Ile Ala Phe Asn Leu Arg Ile Gly Glu Met Lys
    1880             1885             1890

Glu Gly Asp Met Ala Thr Gly Ile Thr Tyr Ala Ser Tyr Gly Tyr
    1895             1900             1905

Phe Cys Gln Met Pro Gln Pro Lys Leu Arg Ala Ala Met Val Glu
    1910             1915             1920

Tyr Ser Phe Ile Phe Leu Asp Glu Tyr His Cys Ala Thr Pro Glu
    1925             1930             1935

Gln Leu Ala Ile Met Gly Lys Ile His Arg Phe Ser Glu Asn Leu
    1940             1945             1950

Arg Val Val Ala Met Thr Ala Thr Pro Ala Gly Thr Val Thr Thr
    1955             1960             1965

Thr Gly Gln Lys His Pro Ile Glu Glu Tyr Ile Ala Pro Glu Val
    1970             1975             1980

Met Lys Gly Glu Asp Leu Gly Ser Glu Tyr Leu Asp Ile Ala Gly
    1985             1990             1995

Leu Lys Ile Pro Val Glu Glu Met Lys Ser Asn Met Leu Val Phe
    2000             2005             2010

Val Pro Thr Arg Asn Met Ala Val Glu Thr Ala Lys Lys Leu Lys
    2015             2020             2025

Ala Lys Gly Tyr Asn Ser Gly Tyr Tyr Tyr Ser Gly Glu Asp Pro
    2030             2035             2040

Ser Asn Leu Arg Val Val Thr Ser Gln Ser Pro Tyr Val Val Val
    2045             2050             2055

Ala Thr Asn Ala Ile Glu Ser Gly Val Thr Leu Pro Asp Leu Asp
    2060             2065             2070

Val Val Val Asp Thr Gly Leu Lys Cys Glu Lys Arg Ile Arg Leu
    2075             2080             2085

Ser Pro Lys Met Pro Phe Ile Val Thr Gly Leu Lys Arg Met Ala
    2090             2095             2100

Val Thr Ile Gly Glu Gln Ala Gln Arg Arg Gly Arg Val Gly Arg
    2105             2110             2115

Val Lys Pro Gly Arg Tyr Tyr Arg Ser Gln Glu Thr Pro Val Gly
    2120             2125             2130

Ser Lys Asp Tyr His Tyr Asp Leu Leu Gln Ala Gln Arg Tyr Gly
    2135             2140             2145

Ile Glu Asp Gly Ile Asn Ile Thr Lys Ser Phe Arg Glu Met Asn
    2150             2155             2160

Tyr Asp Trp Ser Leu Tyr Glu Glu Asp Ser Leu Met Ile Thr Gln
    2165             2170             2175

Leu Glu Ile Leu Asn Asn Leu Leu Ile Ser Glu Glu Leu Pro Met
    2180             2185             2190

Ala Val Lys Asn Ile Met Ala Arg Thr Asp His Pro Glu Pro Ile
    2195             2200             2205

Gln Leu Ala Tyr Asn Ser Tyr Glu Thr Gln Val Pro Val Leu Phe
    2210             2215             2220

Pro Lys Ile Lys Asn Gly Glu Val Thr Asp Ser Tyr Asp Asn Tyr
    2225             2230             2235

Thr Phe Leu Asn Ala Arg Lys Leu Gly Asp Asp Val Pro Pro Tyr
    2240             2245             2250

Val Tyr Ala Thr Glu Asp Glu Asp Leu Ala Val Glu Leu Leu Gly
```

-continued

```
                2255                2260                2265

Leu Asp Trp Pro Asp Pro Gly Asn Gln Gly Thr Val Glu Ala Gly
        2270                2275                2280

Arg Ala Leu Lys Gln Val Val Gly Leu Ser Thr Ala Glu Asn Ala
    2285                2290                2295

Leu Leu Val Ala Leu Phe Gly Tyr Val Gly Tyr Gln Ala Leu Ser
    2300                2305                2310

Lys Arg His Ile Pro Val Val Thr Asp Ile Tyr Ser Ile Glu Asp
    2315                2320                2325

His Arg Leu Glu Asp Thr Thr His Leu Gln Tyr Ala Pro Asn Ala
    2330                2335                2340

Ile Lys Thr Glu Gly Lys Glu Thr Glu Leu Lys Glu Leu Ala Gln
    2345                2350                2355

Gly Asp Val Gln Arg Cys Met Glu Ala Met Thr Asn Tyr Ala Arg
    2360                2365                2370

Asp Gly Ile Gln Phe Met Lys Ser Gln Ala Leu Lys Val Lys Glu
    2375                2380                2385

Thr Pro Thr Tyr Lys Glu Thr Met Asp Thr Val Ala Asp Tyr Val
    2390                2395                2400

Lys Lys Phe Met Glu Ala Leu Ala Asp Ser Lys Glu Asp Ile Ile
    2405                2410                2415

Lys Tyr Gly Leu Trp Gly Thr His Thr Thr Leu Tyr Lys Ser Ile
    2420                2425                2430

Gly Ala Arg Leu Gly Asn Glu Thr Ala Phe Ala Thr Leu Val Val
    2435                2440                2445

Lys Trp Leu Ala Phe Gly Gly Glu Ser Ile Ala Asp His Val Lys
    2450                2455                2460

Gln Ala Ala Thr Asp Leu Val Val Tyr Tyr Ile Ile Asn Arg Pro
    2465                2470                2475

Gln Phe Pro Gly Asp Thr Glu Thr Gln Gln Glu Gly Arg Lys Phe
    2480                2485                2490

Val Ala Ser Leu Leu Val Ser Ala Leu Ala Thr Tyr Thr Tyr Lys
    2495                2500                2505

Ser Trp Asn Tyr Asn Asn Leu Ser Lys Ile Val Glu Pro Ala Leu
    2510                2515                2520

Ala Thr Leu Pro Tyr Ala Ala Thr Ala Leu Lys Leu Phe Ala Pro
    2525                2530                2535

Thr Arg Leu Glu Ser Val Val Ile Leu Ser Thr Ala Ile Tyr Lys
    2540                2545                2550

Thr Tyr Leu Ser Ile Arg Arg Gly Lys Ser Asp Gly Leu Leu Gly
    2555                2560                2565

Thr Gly Val Ser Ala Ala Met Glu Ile Met Ser Gln Asn Pro Val
    2570                2575                2580

Ser Val Gly Ile Ala Val Met Leu Gly Val Gly Ala Val Ala Ala
    2585                2590                2595

His Asn Ala Ile Glu Ala Ser Glu Gln Lys Arg Thr Leu Leu Met
    2600                2605                2610

Lys Val Phe Val Lys Asn Phe Leu Asp Gln Ala Ala Thr Asp Glu
    2615                2620                2625

Leu Val Lys Glu Ser Pro Glu Lys Ile Ile Met Ala Leu Phe Glu
    2630                2635                2640

Ala Val Gln Thr Val Gly Asn Pro Leu Arg Leu Val Tyr His Leu
    2645                2650                2655
```

```
Tyr Gly Val Phe Tyr Lys Gly Trp Glu Ala Lys Glu Leu Ala Gln
2660                2665                2670

Arg Thr Ala Gly Arg Asn Leu Phe Thr Leu Ile Met Phe Glu Ala
2675                2680                2685

Val Glu Leu Leu Gly Val Asp Ser Glu Gly Lys Ile Arg Gln Leu
2690                2695                2700

Ser Ser Asn Tyr Ile Leu Glu Leu Leu Tyr Lys Phe Arg Asp Ser
2705                2710                2715

Ile Lys Ser Ser Val Arg Gln Met Ala Ile Ser Trp Ala Pro Ala
2720                2725                2730

Pro Phe Ser Cys Asp Trp Thr Pro Thr Asp Asp Arg Ile Gly Leu
2735                2740                2745

Pro Gln Asp Asn Phe Leu Arg Val Glu Thr Lys Cys Pro Cys Gly
2750                2755                2760

Tyr Lys Met Lys Ala Val Lys Asn Cys Ala Gly Glu Leu Arg Leu
2765                2770                2775

Leu Glu Glu Glu Gly Ser Phe Leu Cys Arg Asn Lys Phe Gly Arg
2780                2785                2790

Gly Ser Arg Asn Tyr Arg Val Thr Lys Tyr Tyr Asp Asp Asn Leu
2795                2800                2805

Ser Glu Ile Lys Pro Val Ile Arg Met Glu Gly His Val Glu Leu
2810                2815                2820

Tyr Tyr Lys Gly Ala Thr Ile Lys Leu Asp Phe Asn Asn Ser Lys
2825                2830                2835

Thr Ile Leu Ala Thr Asp Lys Trp Glu Val Asp His Ser Thr Leu
2840                2845                2850

Val Arg Val Leu Lys Arg His Thr Gly Ala Gly Tyr Arg Gly Ala
2855                2860                2865

Tyr Leu Gly Glu Lys Pro Asn His Lys His Leu Ile Glu Arg Asp
2870                2875                2880

Cys Ala Thr Ile Thr Lys Asp Lys Val Cys Phe Leu Lys Met Lys
2885                2890                2895

Arg Gly Cys Ala Phe Thr Tyr Asp Leu Ser Leu His Asn Leu Thr
2900                2905                2910

Arg Leu Ile Glu Leu Val His Lys Asn Asn Leu Glu Asp Lys Glu
2915                2920                2925

Ile Pro Ala Val Thr Val Thr Thr Trp Leu Ala Tyr Thr Phe Val
2930                2935                2940

Asn Glu Asp Ile Gly Thr Ile Lys Pro Ala Phe Gly Glu Lys Ile
2945                2950                2955

Thr Pro Glu Met Gln Glu Glu Ile Thr Leu Gln Pro Ala Val Val
2960                2965                2970

Val Asp Ala Thr Asp Val Thr Val Thr Val Gly Glu Thr Pro
2975                2980                2985

Thr Met Thr Thr Gly Glu Thr Pro Thr Thr Phe Thr Ser Ser Gly
2990                2995                3000

Pro Asp Pro Lys Gly Gln Gln Val Leu Lys Leu Gly Val Gly Glu
3005                3010                3015

Gly Gln Tyr Pro Gly Thr Asn Pro Gln Arg Ala Ser Leu His Glu
3020                3025                3030

Ala Ile Gln Ser Ala Asp Glu Arg Pro Ser Val Leu Ile Leu Gly
3035                3040                3045
```

```
Ser Asp Lys Ala Thr Ser Asn Arg Val Lys Thr Val Lys Asn Val
3050                3055                3060

Lys Val Tyr Arg Gly Arg Asp Pro Leu Glu Val Arg Asp Met Met
    3065                3070                3075

Arg Arg Gly Lys Ile Leu Val Ile Ala Leu Ser Arg Val Asp Asn
3080                3085                3090

Ala Leu Leu Lys Phe Val Asp Tyr Lys Gly Thr Phe Leu Thr Arg
    3095                3100                3105

Glu Thr Leu Glu Ala Leu Ser Leu Gly Arg Pro Lys Lys Lys Asn
    3110                3115                3120

Ile Thr Lys Ala Glu Ala Gln Trp Leu Leu Arg Leu Glu Asp Gln
    3125                3130                3135

Met Glu Glu Leu Pro Asp Trp Phe Ala Ala Gly Glu Pro Ile Phe
    3140                3145                3150

Leu Glu Ala Asn Ile Lys His Asp Arg Tyr His Leu Val Gly Asp
    3155                3160                3165

Ile Ala Thr Ile Lys Glu Lys Ala Lys Gln Leu Gly Ala Thr Asp
    3170                3175                3180

Ser Thr Lys Ile Ser Lys Glu Val Gly Ala Lys Val Tyr Ser Met
    3185                3190                3195

Lys Leu Ser Asn Trp Val Met Gln Glu Glu Asn Lys Gln Ser Asn
    3200                3205                3210

Leu Thr Pro Leu Phe Glu Glu Leu Leu Gln Gln Cys Pro Pro Gly
    3215                3220                3225

Gly Gln Asn Lys Thr Ala His Met Val Ser Ala Tyr Gln Leu Ala
    3230                3235                3240

Gln Gly Asn Trp Met Pro Thr Ser Cys His Val Phe Met Gly Thr
    3245                3250                3255

Ile Ser Ala Arg Arg Thr Lys Thr His Pro Tyr Glu Ala Tyr Val
    3260                3265                3270

Lys Leu Arg Glu Leu Val Glu Glu His Lys Met Lys Thr Leu Cys
    3275                3280                3285

Pro Gly Ser Ser Leu Arg Lys His Asn Glu Trp Val Ile Gly Lys
    3290                3295                3300

Ile Lys Tyr Gln Gly Asn Leu Arg Thr Lys His Met Leu Asn Pro
    3305                3310                3315

Gly Lys Val Ala Glu Gln Leu His Arg Glu Gly His Arg His Asn
    3320                3325                3330

Val Tyr Asn Lys Thr Ile Gly Ser Val Met Thr Ala Thr Gly Ile
    3335                3340                3345

Arg Leu Glu Lys Leu Pro Val Val Arg Ala Gln Thr Asp Thr Thr
    3350                3355                3360

Asn Phe His Gln Ala Ile Arg Asp Lys Ile Asp Lys Glu Glu Asn
    3365                3370                3375

Leu Gln Thr Pro Gly Leu His Lys Lys Leu Met Glu Val Phe Asn
    3380                3385                3390

Ala Leu Lys Arg Pro Glu Leu Glu Ser Ser Tyr Asp Ala Val Glu
    3395                3400                3405

Trp Glu Glu Leu Glu Arg Gly Ile Asn Arg Lys Gly Ala Ala Gly
    3410                3415                3420

Phe Phe Glu Arg Lys Asn Ile Gly Glu Ile Leu Asp Ser Glu Lys
    3425                3430                3435

Asn Lys Val Glu Glu Ile Ile Asp Asn Leu Lys Lys Gly Arg Asn
```

-continued

```
            3440                3445                3450
Ile Lys Tyr Tyr Glu Thr Ala Ile Pro Lys Asn Glu Lys Arg Asp
        3455                3460                3465

Val Asn Asp Asp Trp Thr Ala Gly Asp Phe Val Asp Glu Lys Lys
        3470                3475                3480

Pro Arg Val Ile Gln Tyr Pro Glu Ala Lys Thr Arg Leu Ala Ile
        3485                3490                3495

Thr Lys Val Met Tyr Lys Trp Val Lys Gln Lys Pro Val Val Ile
        3500                3505                3510

Pro Gly Tyr Glu Gly Lys Thr Pro Leu Phe Gln Ile Phe Asp Lys
        3515                3520                3525

Val Lys Lys Glu Trp Asp Gln Phe Gln Asn Pro Val Ala Val Ser
        3530                3535                3540

Phe Asp Thr Lys Ala Trp Asp Thr Gln Val Thr Thr Asn Asp Leu
        3545                3550                3555

Glu Leu Ile Lys Asp Ile Gln Lys Tyr Tyr Phe Lys Lys Lys Trp
        3560                3565                3570

His Lys Phe Ile Asp Thr Leu Thr Met His Met Ser Glu Val Pro
        3575                3580                3585

Val Ile Thr Ala Asp Gly Glu Val Tyr Ile Arg Lys Gly Gln Arg
        3590                3595                3600

Gly Ser Gly Gln Pro Asp Thr Ser Ala Gly Asn Ser Met Leu Asn
        3605                3610                3615

Val Leu Thr Met Val Tyr Ala Phe Cys Glu Ala Thr Gly Val Pro
        3620                3625                3630

Tyr Lys Ser Phe Asp Arg Val Ala Lys Ile His Val Cys Gly Asp
        3635                3640                3645

Asp Gly Phe Leu Ile Thr Glu Arg Ala Leu Gly Glu Lys Phe Ala
        3650                3655                3660

Ser Lys Gly Val Gln Ile Leu Tyr Glu Ala Gly Lys Pro Gln Lys
        3665                3670                3675

Ile Thr Glu Gly Asp Lys Met Lys Val Ala Tyr Gln Phe Asp Asp
        3680                3685                3690

Ile Glu Phe Cys Ser His Thr Pro Ile Gln Val Arg Trp Ser Asp
        3695                3700                3705

Asn Thr Ser Ser Tyr Met Pro Gly Arg Asn Thr Thr Thr Ile Leu
        3710                3715                3720

Ala Lys Met Ala Thr Arg Leu Asp Ser Ser Gly Glu Arg Gly Thr
        3725                3730                3735

Ile Ala Tyr Glu Lys Ala Val Ala Phe Ser Phe Leu Leu Met Tyr
        3740                3745                3750

Ser Trp Asn Pro Leu Ile Arg Arg Ile Cys Leu Leu Val Leu Ser
        3755                3760                3765

Thr Glu Leu Gln Val Lys Pro Gly Lys Ser Thr Thr Tyr Tyr Tyr
        3770                3775                3780

Glu Gly Asp Pro Ile Ser Ala Tyr Lys Glu Val Ile Gly His Asn
        3785                3790                3795

Leu Phe Asp Leu Lys Arg Thr Ser Phe Glu Lys Leu Ala Lys Leu
        3800                3805                3810

Asn Leu Ser Met Ser Val Leu Gly Ala Trp Thr Arg His Thr Ser
        3815                3820                3825

Lys Arg Leu Leu Gln Asp Cys Val Asn Met Gly Val Lys Glu Gly
        3830                3835                3840
```

```
Asn Trp Leu Val Asn Ala Asp Arg Leu Val Ser Ser Lys Thr Gly
3845                3850                3855

Asn Arg Tyr Val Pro Gly Glu Gly His Thr Leu Gln Gly Arg His
3860                3865                3870

Tyr Glu Glu Leu Val Leu Ala Arg Lys Gln Ile Asn Ser Phe Gln
3875                3880                3885

Gly Thr Asp Arg Tyr Asn Leu Gly Pro Ile Val Asn Met Val Leu
3890                3895                3900

Arg Arg Leu Arg Val Met Met Met Thr Leu Ile Gly Arg Gly Val
3905                3910                3915

<210> SEQ ID NO 3
<211> LENGTH: 12357
<212> TYPE: DNA
<213> ORGANISM: Classical Swine Fever Virus

<400> SEQUENCE: 3
```

| | | | | | |
|---|---|---|---|---|---|
| gtatacgagg | ttagttcatt | ctcgtgtaca | tgattggaca | aatcaaaatc | tcaatttggt | 60
| tcagggcctc | cctccagcga | cggccgagct | gggctagcca | tgcccacagt | aggactagca | 120
| aacgaggga | ctagccgtag | tggcgagctc | cctgggtggt | ctaagtcctg | agtacaggac | 180
| agtcgtcagt | agttcgacgt | gagcagaagc | ccacctcgag | atgctatgtg | acgagggca | 240
| tgcccaagac | acaccttaac | cctagcgggg | gtcgttaggg | tgaaatcaca | ccatgtgatg | 300
| ggagtacgac | ctgatagggt | gctgcagagg | cccactatta | ggctagtata | aaaatctctg | 360
| ctgtacatgg | cacatggagt | tgaatcattt | tgaactttta | tacaaaacaa | acaaacaaaa | 420
| accaatggga | gtggaggaac | cggtatacga | tgtaacgggg | agaccattgt | ttggagaccc | 480
| aagtgaggta | cacccacaat | caacattgaa | gctaccacat | gatagggga | gaggcaacat | 540
| caaaacaaca | ctgaagaacc | tacctaggag | aggtgactgc | aggagtggca | accacctagg | 600
| cccggttagt | gggatatatg | taaagcccgg | ccctgtcttt | tatcaggact | acatgggccc | 660
| agtctatcat | agagcccctc | tagagttttt | tgacgaagca | cagttttgtg | aggtgaccaa | 720
| aaggataggt | agggtgacag | gtagtgacgg | aaagctttac | catatatacg | tgtgcatcga | 780
| tggttgcatc | ctgctgaagc | tagccaagag | gggcgagcca | agaaccctga | agtggattag | 840
| aaatctcacc | gactgtccat | tgtgggttac | cagttgttct | gatgatggtg | caagtgcaag | 900
| taaagagaag | aaaccagata | ggatcaacaa | gggtaaatta | agatagccc | caaagagca | 960
| tgagaaggac | agcaggacta | agccacctga | tgctacgatt | gtagtggaag | gagtaaaata | 1020
| ccaggtcaaa | aagaaaggta | aagttaaggg | aaagaatacc | caagacggcc | tgtaccacaa | 1080
| caagaataaa | ccaccagaat | ctaggaagaa | attagaaaaa | gccctattgg | catgggcagt | 1140
| gatagcaatt | atgttatacc | aacctgttgc | agccgaaaat | ataactcaat | ggaacctgag | 1200
| tgacaacggt | accaatggta | tccagcacgc | tatgtaccct | agaggagtca | gcagaagctt | 1260
| gcatgggatc | tggccagaaa | aaatatgcaa | aggagtcccc | acctacctgg | ccacagacac | 1320
| ggaactgaga | gaaatacagg | gaatgatgga | tgccagcgag | gggacaaact | atacgtgctg | 1380
| taagttacag | agacatgaat | ggaacaaaca | tggatggtgt | aactggtata | acatagaccc | 1440
| ctggatacag | ttgatgaata | gaacccaagc | aaacttggca | gaaggccctc | cgagcaagga | 1500
| gtgcgccgtg | acttgcaggt | acgataaaaa | tgctgacatt | aacgtggtca | cccaggccag | 1560
| aaacaggcca | accaccctaa | ctggctgcaa | gaaagggaaa | attttttctt | ttgcgggtac | 1620
| agttatagag | ggcccatgta | atttcaacgt | ttctgttgag | gatatcttat | atgggatca | 1680

```
tgagtgtggc agtctactcc aggatacggc tctataccta gtagatggaa tgaccaacac    1740
tatagagaga gccaggcagg gagccgcgag ggtgacatct tggctaggga ggcaactcag    1800
aactgccggg aagaggttgg agggcagaag caaaacctgg tttggtgcct atgccctatc    1860
accttattgt aatgtgacaa gcaaaatagg gtacatatgg tacactaaca actgtacccc    1920
ggcttgcctc cccaaaaata caaagataat aggccccggt aaatttgaca ctaacgcgga    1980
agacggaaag attctccatg agatggggggg ccacctatca gaatttctgc tgctctctct    2040
ggtcgttctg tctgacttcg cccctgaaac agccagcgcg ttatacctca ttttgcacta    2100
cgtgatccct caatcccatg aagaacctga aggctgtgac acaaaccagc tgaatttaac    2160
agtggaactc aggactgaag acgtgatacc atcatcagtc tggaatgttg gcaaatatgt    2220
gtgtgttaga ccagactggt ggccatatga accaaggtg ctttgttat ttgaagaggc       2280 aggacaggtc gtaaagttag ccttgcgggc actgagggat ttaaccaggg tctggaatag    2340
cgcatcaacc acggcattcc tcatctgctt gataaaagta ttaagaggac aggtcgtgca    2400
aggtgtgata tggctgttac tggtaactgg ggcacctgtc tcttgtacac atcttgcggc    2460
cgcagattac aaggatgacg acgataaggg ggcacaaggc cggctagcct gcaaggaaga    2520
tcacaggtac gctatatcaa caaccaatga gatagggcta cttggggccg aaggtctcac    2580
taccacctgg aaagaataca accacaattt gcaactggat gatgggaccg tcaaggccat    2640
ctgcatggca ggttccttta agtcacagc acttaatgtg gttagtagga ggtatctggc     2700
atcattacat aaggacgctt tacccacttc cgtgacattc gagctcctgt tcgacgggac    2760
cagcccattg accgaggaaa tgggagatga cttcgggttc ggactgtgtc cgtatgatac    2820
gagccctgta gtcaagggaa agtacaacac aaccttgttg aatggtagtg cattctacct    2880
agtttgccca ataggggtgga cgggtgttat agagtgcacg tcatttaata tggacactct    2940
gagaacagaa gtggtaaaga ccttcagaag agagaaaccc tttccgtaca aagggattg    3000 tgtgaccact acagtggaaa atgaagatct attctactgt aaatgggggg gcaattggac    3060
atgtgtgaaa ggtgaaccag tgacctacac gggggggcca gtaaaacaat gcagatggtg    3120
tggcttcgac ttcaatgagc ctgacggact cccacactac cccataggta agtgcatttt    3180
ggcaaatgag acaggttaca gaatagtgga ttcaacggac tgtaacagag atggcgttgt    3240
aatcagcaca gaggggagtc atgagtgctt gattggtaac acaactgtca aggtgcatgc    3300
attagatgaa agactaggcc ctatgccatg caggcctaag gagatcgtct ctagtgcggg    3360
acctgtaagg aaaacttcct gtacattcaa ctacgcaaaa actctgagga caggtattaa   3420
tgagcccagg gacagctatt ccaacaata tatgctcaag ggcgagtatc agtactggtt     3480
tgatctggat gtgaccgacc gccactcaga ttacttcgca gaattcattg tcttggtggt    3540
ggtggcactg ttgggaggaa gatatgtcct gtggctaata gtgacctaca gttctaac     3600 agaacaactc gccgctggtc tacagttagg ccagggtgag gtagtgttaa tagggaactt   3660
aatcacccac acagatattg aggttgtagt atatttctta ctgctctatt tggtcatgag    3720
agatgagcct ataaagaaat ggatactact gctgttccat gctatgacca acaatccagt    3780
taagaccata acagtggcac tgctcatggt tagcgggggtt gccaagggtg aaagataga    3840 tggtggttgg cagcggctgc cggagaccaa ctttgatatc caactcgcgc tgacagttat    3900
agtagtcgct gtgatgttgc tggcaaagaa agatccgact accgtcccct tggttataac    3960
ggtggcaacc ctgagaacgg ctaagataac taatggactt agtacagatc tagccatagc    4020
```

```
tacagtgtca acagctttgc taacctggac ctacattagt gactattata aatacaagac    4080
cttgctacag taccttatta gcacagtgac aggtatcttc ttgataaggg tactgaaggg    4140
ggtaggtgag ttagatttac acccccaac cttaccatct tacagacccc tcttcttcat    4200
cctcgtgtac ctcatttcca ctgcagtggt aacaagatgg aatctggaca tagccggatt    4260
gctgctgcag tgtgtcccaa ccctttaat ggttttcacg atgtgggcag acatccttac    4320
cctgatcctc atactgccta cttacgagtt gacaaaacta tattacctca aggaagtgaa    4380
gattggggca gaaaggggct ggttgtggaa gaccaacttc aagagggtaa atgacatata    4440
cgaagttgac caagctggtg aggggtgta ccttttccca tcaaaacaaa agacaggtac    4500
aataacaggt actatgttgc cattgatcaa agccatactc ataagttgca tcagcaataa    4560
gtggcaattt atatatctat tgtacttgat attcgaagtg tcttactacc ttcacaagaa    4620
gatcatagat gaaatagcag gagggaccaa cttcatctcg agacttgtag ccgctctgat    4680
tgaagccaat tgggcctttg caacgaaga agttagaggt ttaaagaagt tcttcctgct    4740
gtctagtagg gttaaagaac tgatcatcaa acacaaagtg aggaatgaag tgatggtcca    4800
ctggtttggc gacgaagagg tctatgggat gccgaagctg gttggcttag tcaaggcagc    4860
aacactgagt aaaaataaac attgtattt gtgcaccgtc tgtgaaaaca gagagtggag    4920
aggagaaacc tgcccaaaat gcggccgttt tgggccacca gtgacctgtg catgaccct    4980 agccgacttt gaagaaaaac actataagag gatttctttt agagaggatc aatcagaagg    5040
gccggttagg gaggagtatg cagggtatct gcaatataga gccagagggc aattattcct    5100
gaggaatctc ccggtgctag caacaaagt caagatgctc ctggtcggaa atcttgggac    5160
ggaggtgggg gatttggaac accttggctg ggtgctcaga gggcctgccg tttgcaagaa    5220
ggttaccgaa catgagaaat gcaccacatc cataatggac aaattaactg ctttcttcgg    5280
tgttatgcca aggggcacca cacctagagc ccctgtgaga ttccccacct ctctcttaaa    5340
gataagaagg gggctggaaa ctggctgggc gtacacacac caaggtggca tcagttcagt    5400
ggaccatgtc acttgtggga aagacttact ggtatgtgac actatgggcc ggacaagggt    5460
tgtttgccaa tcaaataaca agatgacaga cgagtccgag tatggagtta aaactgactc    5520
cggatgcccg gagggagcta ggtgttacgt gttcaaccca gaggcagtta acatatccgg    5580
gactaaagga gccatggtcc acttacaaaa aactggagga gaattcacct gtgtgacagc    5640
atcagggact ccggccttct tgatctcaa gaacctcaaa ggctggtcag gctgccgat    5700 atttgaggca tcaagtggaa gagtagtcgg cagggttaag gtcgggaaga atgaggactc    5760
taaaccaacc aagcttatga gtggaataca aacagtctcc aaaagtacca cagacttgac    5820
agaaatggta aagaaaataa caaccatgaa caggggagaa ttcagacaaa taacccttgc    5880
cacaggtgcc ggaaaaacca cggaactccc tagatcagtc atagaagaga taggaaggca    5940
taagagggtc ttggtcttga tccctctgag ggcggcagca gagtcagtat accaatatat    6000
gagacaaaaa cacccaagca tagcattcaa cttgaggata gggagatga aggaagggga    6060 catggccaca gggataacct atgcctcata tggttacttc tgtcagatgc cacaacctaa    6120
gctgcgagcc gcgatggttg agtactcctt catattcctt gatgagtacc actgtgccac    6180
ccccgaacaa ttggctatca tgggaaagat ccacagattt tcagagaacc tgcgggtagt    6240
agccatgacc gcaacaccag caggcacggt aacaactaca gggcaaaaac accctataga    6300
agaatacata gccccagaag tgatgaaggg ggaagactta ggttcagagt acttggacat    6360
agctggacta aagataccag tagaggagat gaagagtaac atgctggtct ttgtgcccac    6420
```

```
aaggaacatg gctgtagaga cggcaaagaa actgaaagct aagggttata actcaggcta   6480
ctattatagt ggagaggatc catctaacct gagggtggta acatcacagt ccccgtacgt   6540
ggtggtagca accaacgcaa tagaatcagg tgttactctc ccagacttgg atgtggtcgt   6600
cgacacaggg cttaagtgtg aaaagaggat acggctgtca cctaagatgc ccttcatagt   6660
gacgggcctg aagagaatgg ctgtcacgat tggggaacaa gcccagagaa ggggggagagt   6720 tgggagagtg aagcctggga gatactacag gagtcaagaa accccgttg gttccaaaga   6780 ttaccattac gacctactgc aagcacagag gtacggtata aagatgggga taaacatcac   6840
caaatctttt agagagatga attatgattg gagcctttat gaggaggata gtctgatgat   6900
tacacaattg gaaatcctca acaatctgtt gatatcagaa gagctaccaa tggcagtaaa   6960
aaatataatg gccaggactg accacccaga accaatccaa ctggcgtaca acagctacga   7020
aacgcaggtg ccagtgctat tcccaaaaat aaaaaatgga gaggtgactg acagttacga   7080
taactatacc ttcctcaacg caagaaagct ggggggatgat gtacctccct acgtgtatgc   7140
cacagaggat gaggacttag cggtagagct gctgggctta gactggccgg accctgggaa   7200
ccaaggaacc gtggaggctg gtagagcact aaaacaagta gttggtctat caacagctga   7260
gaacgccctg ttagtagctt tattcggcta tgtaggatat caggcactct caaagaggca   7320
tataccagta gtcacagaca tatattcaat tgaagatcac aggttggaag acaccacaca   7380
cctacagtat gccccgaatg ctatcaagac ggaggggaag gagacagaat tgaaggagct   7440
agctcagggg gatgtgcaga gatgtatgga agctatgact aattatgcaa gagatggcat   7500
ccaattcatg aagtctcagg cactgaaagt gaaagaaacc cccacttaca agagacaat   7560 ggacaccgtg gcggactatg taaagaagtt catggaggca ctggcggaca gcaaagaaga   7620
catcataaaa tatgggttgt gggggacgca cacaacctta tataagagca tcggtgctag   7680
gcttgggaac gagactgcgt tcgctacccct ggtcgtgaaa tggctggcat ttggggggaga   7740 atcaatagca gaccatgtca aacaagcggc cacagacttg gtcgtttact atatcatcaa   7800
cagacctcag ttcccaggag acacggggac acaacaggaa ggaaggaaat ttgtagccag   7860
cctactggtc tcagccctgg ctacttacac ttacaaaagc tggaattaca ataatctgtc   7920
caagatagtt gaaccggctt tggctactct gccctatgcc gccacagctc tcaagctatt   7980
cgcccccact cgattggaga gcgttgtcat actgagtacc gcaatctaca aaacctacct   8040
atcaatcagg cgcggaaaaa gcgatggttt gctaggcaca ggggttagtg cggctatgga   8100
aatcatgtca caaaacccag tatctgtggg tatagcggtc atgctagggg tggggggcgt   8160
agcggcccac aatgcaatcg aagccagtga gcagaagaga acactactca tgaaagtttt   8220
tgtaaagaac ttcttggatc aggcagccac tgatgaatta gtcaaggaga gccctgagaa   8280
aataataatg gcttttgtttg aagcagtgca gacagtcggc aaccctctta gactggtata   8340
ccacctttac ggagtttttt acaaagggtg ggaagcaaaa gagttggccc aaaggacagc   8400
cggtaggaat cttttcactt tgataatgtt tgaggctgtg aactactgg gagtagatag   8460 cgaaggaaag atccgccagc tatcaagcaa ttacatacta gagctcctgt ataagttccg   8520
tgacagtatc aagtccagcg tgaggcagat ggcaatcagc tgggcccctg ccccttttag   8580
ttgtgattgg acaccgacgg atgcagaat agggcttccc caagataatt tcctccgagt   8640
ggagacaaaa tgcccctgtg gttacaagat gaaagcagtt aagaattgtg ctggggagtt   8700
gagactctta gaagaggaag gctcatttct ctgcaggaat aaattcggga gaggttcacg   8760
```

```
gaactacagg gtgacaaaat actatgatga caatctatca gaaataaagc cagtgataag    8820
aatggaagga catgtggaac tctactacaa gggagccact attaaactgg atttcaacaa    8880
cagtaaaaca atattggcaa ccgataaatg ggaggtcgat cactccactc tggtcagggt    8940
gctcaagagg cacacagggg ctggatatcg tggggcatac ctgggtgaga aaccgaacca    9000
caaacatctg atagagaggg actgcgcaac catcaccaaa gataaggttt gttttctcaa    9060
gatgaagaga gggtgtgcat ttacttatga cttatccctt cacaacctta cccggctgat    9120
cgaattggta cacaagaata acttggaaga caaagagatt cctgccgtta cggtcacaac    9180
ctggctggct tacacatttg taaatgaaga tatagggacc ataaaaccag ccttcgggga    9240
gaaaataaca ccagagatgc aggaggagat aaccttgcag cctgctgtag tggtggatgc    9300
aactgacgtg accgtgaccg tggtagggga accccctact atgactacag gggagacccc    9360
aacaacgttc accagctcag gtccagaccc gaaaggccaa caagttttaa aactgggagt    9420
aggtgaaggc caatacccg ggactaatcc acagagagca agcctgcacg aagccataca    9480
aagcgcagat gaaaggccct ctgtgttgat attggggtct gataaagcca cctctaatag    9540
agtgaaaact gtaaagaatg tgaaggtata cagaggcagg gacccactag aagtgagaga    9600
tatgatgagg aggggaaaga tcctagtcat agccctgtct agggttgata atgctctatt    9660
gaaatttgta gattacaaag gcacctttct aactagagag accctggagg cattaagttt    9720
gggtaggcca aaaagaaaa acataaccaa ggcagaagca cagtggttgc tgcgcctcga    9780
agaccaaatg gaagagctac ccgattggtt cgcagccggg gaacccattt ttttagaggc    9840
caatattaaa catgacaggt atcatctggt agggatata gctactatca aagagaaagc    9900
caaacaattg ggggctacag actctacaaa gatatccaag gaggttggtg caaaagtata    9960
ttctatgaaa ttgagtaatt gggtgatgca agaagaaaac aaacagagca acttgacccc   10020
cttatttgaa gagctcctac agcagtgtcc acccggaggc caaaacaaaa ctgcacatat   10080
ggtctctgct taccaactag ctcaaggaa ctggatgcca accagctgcc atgttttat   10140 ggggaccata tctgccagaa ggactaagac ccatccatat gaagcatatg tcaagttaag   10200
ggagttggta gaggaacaca agatgaaaac attgtgtccc ggatcaagtc tgcgtaagca   10260
caatgaatgg gtaattggca agatcaaata ccagggcaac ctgaggacca acacatgtt   10320 gaaccccggc aagtggcag agcaactgca cagagaagga cacagacaca atgtgtataa   10380
caagacaata ggctcagtga tgacagctac tggcatcagg ttggagaagt tgcccgtggt   10440
tagggcccag acagacacaa ccaacttcca ccaagcaata agggataaga tagacaagga   10500
agagaatcta cagaccccgg gtttacataa gaaactaatg gaagttttca atgcattgaa   10560
acgacccgag ttagagtcct cctatgacgc tgtggaatgg gaggaattgg agagaggaat   10620
aaacagaaag ggtgctgctg gtttctttga acgcaaaaac ataggggaga tattggattc   10680
agagaaaaat aaagtagaag agattattga caatctgaaa agggtagaa atatcaaata   10740 ctatgaaacc gcaatcccaa aaaatgaaaa gagggatgtc aatgatgact ggaccgcagg   10800
tgactttgtg gacgagaaga acccagagtt catacaatac cctgaagcaa aaacaaggct   10860
ggccatcacc aagtgatgt ataagtgggg gaagcagaag ccagtagtca tacccggta   10920 tgaagggaag acacctctgt tccaaatttt tgacaaagta agaaggaat gggatcaatt   10980 ccaaaatcca gtggcagtga gcttcgacac taaggcgtgg gacacccagg tgaccacaaa   11040
tgatctggag ctgataaagg acatacaaaa gtactacttc aagaagaaat ggcataaatt   11100
tattgacacc ctgactatgc atatgtcaga agtacccgta atcactgctg atgggagggt   11160
```

```
gtatataagg aaagggcaaa gaggtagtgg acagcccgac acaagcgcag gcaacagcat  11220
gctaaatgtg ttaacaatgg tttatgcctt ctgcgaggcc acaggggtac cctacaagag  11280
ttttgacagg gtggcaaaaa ttcatgtgtg cggggacgat ggtttcctga tcacagagag  11340
agctctcggc gagaaattcg caagcaaggg agtccaaatc ctgtatgaag ctgggaagcc  11400
ccagaagatc actgaagggg acaaaatgaa agtggcctac caatttgatg atattgagtt  11460
ttgctcccat acaccaatac aagtaaggtg gtcagataac acttctagct acatgccagg  11520
gagaaataca accacaatcc tggctaaaat ggccacaagg ttagattcca gtggtgagag  11580
gggtaccata gcgtacgaga aagcagtagc attcagcttc ctgctaatgt attcctggaa  11640
cccactaatc agaaggattt gcttattggt actatcaact gaactgcaag tgaaaccagg  11700
gaagtcaacc acttactatt atgaagggga cccgatatct gcctacaagg aagtcatcgg  11760
ccacaatctt ttcgatctca agagaacaag cttcgagaag ctggccaagt aaatctcag  11820 catgtccgta ctcgggcct ggactagaca caccagcaaa agactactac aagactgtgt  11880
caatatgggt gttaaagagg gcaactggtt agtcaatgca gacagactgg tgagtagtaa  11940
gactggaaat aggtatgtac ctggagaagg ccacaccctg caagggagac attatgaaga  12000
actggtgttg gcaagaaaac agatcaacag cttccaaggg acagacaggt acaatctagg  12060
cccaatagtc aacatggtgt taaggaggct gagagtcatg atgatgaccc tgataggggag  12120 aggggtatga gtgcgggtga cccgcgatct ggacccgtca gtaggaccct attgtagata  12180
acactaattt tttattttat tagatattac tatttattta tttatttatt tattgaatga  12240
gtaagaactg gtacaaacta cctcatgtta ccacactaca ctcattttaa cagcacttta  12300
gctggaagga aaattcctga cgtccacagt tggactaagg taatttccta acggccc    12357
```

<210> SEQ ID NO 4
<211> LENGTH: 3918
<212> TYPE: PRT
<213> ORGANISM: Classical Swine Fever Virus

<400> SEQUENCE: 4

```
Met Glu Leu Asn His Phe Glu Leu Leu Tyr Lys Thr Asn Lys Gln Lys
1               5                   10                  15

Pro Met Gly Val Glu Glu Pro Val Tyr Asp Val Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Arg Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Ile Asp Gly Cys Ile Leu Leu Lys Leu Ala
    130                 135                 140

Lys Arg Gly Glu Pro Arg Thr Leu Lys Trp Ile Arg Asn Leu Thr Asp
145                 150                 155                 160
```

```
Cys Pro Leu Trp Val Thr Ser Cys Ser Asp Gly Ala Ser Ala Ser
                165                 170                 175
Lys Glu Lys Lys Pro Asp Arg Ile Asn Lys Gly Lys Leu Lys Ile Ala
            180                 185                 190
Pro Lys Glu His Glu Lys Asp Ser Arg Thr Lys Pro Pro Asp Ala Thr
            195                 200                 205
Ile Val Val Glu Gly Val Lys Tyr Gln Val Lys Lys Gly Lys Val
210                 215                 220
Lys Gly Lys Asn Thr Gln Asp Gly Leu Tyr His Asn Lys Asn Lys Pro
225                 230                 235                 240
Pro Glu Ser Arg Lys Lys Leu Glu Lys Ala Leu Leu Ala Trp Ala Val
            245                 250                 255
Ile Ala Ile Met Leu Tyr Gln Pro Val Ala Ala Glu Asn Ile Thr Gln
            260                 265                 270
Trp Asn Leu Ser Asp Asn Gly Thr Asn Gly Ile Gln His Ala Met Tyr
            275                 280                 285
Leu Arg Gly Val Ser Arg Ser Leu His Gly Ile Trp Pro Glu Lys Ile
            290                 295                 300
Cys Lys Gly Val Pro Thr Tyr Leu Ala Thr Asp Thr Glu Leu Arg Glu
305                 310                 315                 320
Ile Gln Gly Met Met Asp Ala Ser Glu Gly Thr Asn Tyr Thr Cys Cys
                325                 330                 335
Lys Leu Gln Arg His Glu Trp Asn Lys His Gly Trp Cys Asn Trp Tyr
            340                 345                 350
Asn Ile Asp Pro Trp Ile Gln Leu Met Asn Arg Thr Gln Ala Asn Leu
            355                 360                 365
Ala Glu Gly Pro Pro Ser Lys Glu Cys Ala Val Thr Cys Arg Tyr Asp
            370                 375                 380
Lys Asn Ala Asp Ile Asn Val Val Thr Gln Ala Arg Asn Arg Pro Thr
385                 390                 395                 400
Thr Leu Thr Gly Cys Lys Lys Gly Lys Asn Phe Ser Phe Ala Gly Thr
            405                 410                 415
Val Ile Glu Gly Pro Cys Asn Phe Asn Val Ser Val Glu Asp Ile Leu
            420                 425                 430
Tyr Gly Asp His Glu Cys Gly Ser Leu Leu Gln Asp Thr Ala Leu Tyr
            435                 440                 445
Leu Val Asp Gly Met Thr Asn Thr Ile Glu Arg Ala Arg Gln Gly Ala
            450                 455                 460
Ala Arg Val Thr Ser Trp Leu Gly Arg Gln Leu Arg Thr Ala Gly Lys
465                 470                 475                 480
Arg Leu Glu Gly Arg Ser Lys Thr Trp Phe Gly Ala Tyr Ala Leu Ser
            485                 490                 495
Pro Tyr Cys Asn Val Thr Ser Lys Ile Gly Tyr Ile Trp Tyr Thr Asn
            500                 505                 510
Asn Cys Thr Pro Ala Cys Leu Pro Lys Asn Thr Lys Ile Ile Gly Pro
            515                 520                 525
Gly Lys Phe Asp Thr Asn Ala Glu Asp Gly Lys Ile Leu His Glu Met
            530                 535                 540
Gly Gly His Leu Ser Glu Phe Leu Leu Leu Ser Leu Val Val Leu Ser
545                 550                 555                 560
Asp Phe Ala Pro Glu Thr Ala Ser Ala Leu Tyr Leu Ile Leu His Tyr
            565                 570                 575
Val Ile Pro Gln Ser His Glu Glu Pro Glu Gly Cys Asp Thr Asn Gln
```

```
                580             585             590
Leu Asn Leu Thr Val Glu Leu Arg Thr Glu Asp Val Ile Pro Ser Ser
            595                 600             605
Val Trp Asn Val Gly Lys Tyr Val Cys Val Arg Pro Asp Trp Trp Pro
            610             615                 620
Tyr Glu Thr Lys Val Ala Leu Leu Phe Glu Glu Ala Gly Gln Val Val
625                     630             635                 640
Lys Leu Ala Leu Arg Ala Leu Arg Asp Leu Thr Arg Val Trp Asn Ser
                    645             650                 655
Ala Ser Thr Thr Ala Phe Leu Ile Cys Leu Ile Lys Val Leu Arg Gly
                660             665             670
Gln Val Val Gln Gly Val Ile Trp Leu Leu Leu Val Thr Gly Ala Pro
            675             680             685
Val Ser Cys Thr His Leu Ala Ala Ala Asp Tyr Lys Asp Asp Asp Asp
            690             695             700
Lys Gly Ala Gln Gly Arg Leu Ala Cys Lys Glu Asp His Arg Tyr Ala
705                 710             715                 720
Ile Ser Thr Thr Asn Glu Ile Gly Leu Leu Gly Ala Glu Gly Leu Thr
                    725             730                 735
Thr Thr Trp Lys Glu Tyr Asn His Asn Leu Gln Leu Asp Asp Gly Thr
                740             745             750
Val Lys Ala Ile Cys Met Ala Gly Ser Phe Lys Val Thr Ala Leu Asn
                755             760             765
Val Val Ser Arg Arg Tyr Leu Ala Ser Leu His Lys Asp Ala Leu Pro
770                 775             780
Thr Ser Val Thr Phe Glu Leu Leu Phe Asp Gly Thr Ser Pro Leu Thr
785                 790             795                 800
Glu Glu Met Gly Asp Asp Phe Gly Phe Gly Leu Cys Pro Tyr Asp Thr
                    805             810             815
Ser Pro Val Val Lys Gly Lys Tyr Asn Thr Thr Leu Leu Asn Gly Ser
                820             825             830
Ala Phe Tyr Leu Val Cys Pro Ile Gly Trp Thr Gly Val Ile Glu Cys
                835             840             845
Thr Ser Phe Asn Met Asp Thr Leu Arg Thr Glu Val Val Lys Thr Phe
                850             855             860
Arg Arg Glu Lys Pro Phe Pro Tyr Arg Arg Asp Cys Val Thr Thr Thr
865                 870             875                 880
Val Glu Asn Glu Asp Leu Phe Tyr Cys Lys Trp Gly Asn Trp Thr
                    885             890                 895
Cys Val Lys Gly Glu Pro Val Thr Tyr Thr Gly Gly Pro Val Lys Gln
                    900             905             910
Cys Arg Trp Cys Gly Phe Asp Phe Asn Glu Pro Asp Gly Leu Pro His
            915             920             925
Tyr Pro Ile Gly Lys Cys Ile Leu Ala Asn Glu Thr Gly Tyr Arg Ile
            930             935             940
Val Asp Ser Thr Asp Cys Asn Arg Asp Gly Val Val Ile Ser Thr Glu
945                     950             955                 960
Gly Ser His Glu Cys Leu Ile Gly Asn Thr Thr Val Lys Val His Ala
                    965             970             975
Leu Asp Glu Arg Leu Gly Pro Met Pro Cys Arg Pro Lys Glu Ile Val
            980             985             990
Ser Ser Ala Gly Pro Val Arg Lys  Thr Ser Cys Thr Phe Asn Tyr Ala
            995                 1000            1005
```

```
Lys Thr Leu Arg Asn Arg Tyr Tyr Glu Pro Arg Asp Ser Tyr Phe
    1010            1015            1020

Gln Gln Tyr Met Leu Lys Gly Glu Tyr Gln Tyr Trp Phe Asp Leu
    1025            1030            1035

Asp Val Thr Asp Arg His Ser Asp Tyr Phe Ala Glu Phe Ile Val
    1040            1045            1050

Leu Val Val Val Ala Leu Leu Gly Gly Arg Tyr Val Leu Trp Leu
    1055            1060            1065

Ile Val Thr Tyr Ile Val Leu Thr Glu Gln Leu Ala Ala Gly Leu
    1070            1075            1080

Gln Leu Gly Gln Gly Glu Val Val Leu Ile Gly Asn Leu Ile Thr
    1085            1090            1095

His Thr Asp Ile Glu Val Val Tyr Phe Leu Leu Leu Tyr Leu
    1100            1105            1110

Val Met Arg Asp Glu Pro Ile Lys Lys Trp Ile Leu Leu Leu Phe
    1115            1120            1125

His Ala Met Thr Asn Asn Pro Val Lys Thr Ile Thr Val Ala Leu
    1130            1135            1140

Leu Met Val Ser Gly Val Ala Lys Gly Gly Lys Ile Asp Gly Gly
    1145            1150            1155

Trp Gln Arg Leu Pro Glu Thr Asn Phe Asp Ile Gln Leu Ala Leu
    1160            1165            1170

Thr Val Ile Val Val Ala Val Met Leu Leu Ala Lys Lys Asp Pro
    1175            1180            1185

Thr Thr Val Pro Leu Val Ile Thr Val Ala Thr Leu Arg Thr Ala
    1190            1195            1200

Lys Ile Thr Asn Gly Leu Ser Thr Asp Leu Ala Ile Ala Thr Val
    1205            1210            1215

Ser Thr Ala Leu Leu Thr Trp Thr Tyr Ile Ser Asp Tyr Tyr Lys
    1220            1225            1230

Tyr Lys Thr Leu Leu Gln Tyr Leu Ile Ser Thr Val Thr Gly Ile
    1235            1240            1245

Phe Leu Ile Arg Val Leu Lys Gly Val Gly Glu Leu Asp Leu His
    1250            1255            1260

Thr Pro Thr Leu Pro Ser Tyr Arg Pro Leu Phe Phe Ile Leu Val
    1265            1270            1275

Tyr Leu Ile Ser Thr Ala Val Val Thr Arg Trp Asn Leu Asp Ile
    1280            1285            1290

Ala Gly Leu Leu Leu Gln Cys Val Pro Thr Leu Leu Met Val Phe
    1295            1300            1305

Thr Met Trp Ala Asp Ile Leu Thr Leu Ile Leu Ile Leu Pro Thr
    1310            1315            1320

Tyr Glu Leu Thr Lys Leu Tyr Tyr Leu Lys Glu Val Lys Ile Gly
    1325            1330            1335

Ala Glu Arg Gly Trp Leu Trp Lys Thr Asn Phe Lys Arg Val Asn
    1340            1345            1350

Asp Ile Tyr Glu Val Asp Gln Ala Gly Glu Gly Val Tyr Leu Phe
    1355            1360            1365

Pro Ser Lys Gln Lys Thr Gly Thr Ile Thr Gly Thr Met Leu Pro
    1370            1375            1380

Leu Ile Lys Ala Ile Leu Ile Ser Cys Ile Ser Asn Lys Trp Gln
    1385            1390            1395
```

-continued

```
Phe Ile Tyr Leu Leu Tyr Leu Ile Phe Glu Val Ser Tyr Tyr Leu
1400                1405                1410

His Lys Lys Ile Ile Asp Glu Ile Ala Gly Gly Thr Asn Phe Ile
1415                1420                1425

Ser Arg Leu Val Ala Ala Leu Ile Glu Ala Asn Trp Ala Phe Asp
1430                1435                1440

Asn Glu Glu Val Arg Gly Leu Lys Lys Phe Phe Leu Leu Ser Ser
1445                1450                1455

Arg Val Lys Glu Leu Ile Ile Lys His Lys Val Arg Asn Glu Val
1460                1465                1470

Met Val His Trp Phe Gly Asp Glu Glu Val Tyr Gly Met Pro Lys
1475                1480                1485

Leu Val Gly Leu Val Lys Ala Ala Thr Leu Ser Lys Asn Lys His
1490                1495                1500

Cys Ile Leu Cys Thr Val Cys Glu Asn Arg Glu Trp Arg Gly Glu
1505                1510                1515

Thr Cys Pro Lys Cys Gly Arg Phe Gly Pro Pro Val Thr Cys Gly
1520                1525                1530

Met Thr Leu Ala Asp Phe Glu Glu Lys His Tyr Lys Arg Ile Phe
1535                1540                1545

Phe Arg Glu Asp Gln Ser Glu Gly Pro Val Arg Glu Glu Tyr Ala
1550                1555                1560

Gly Tyr Leu Gln Tyr Arg Ala Arg Gly Gln Leu Phe Leu Arg Asn
1565                1570                1575

Leu Pro Val Leu Ala Thr Lys Val Lys Met Leu Leu Val Gly Asn
1580                1585                1590

Leu Gly Thr Glu Val Gly Asp Leu Glu His Leu Gly Trp Val Leu
1595                1600                1605

Arg Gly Pro Ala Val Cys Lys Lys Val Thr Glu His Glu Lys Cys
1610                1615                1620

Thr Thr Ser Ile Met Asp Lys Leu Thr Ala Phe Phe Gly Val Met
1625                1630                1635

Pro Arg Gly Thr Thr Pro Arg Ala Pro Val Arg Phe Pro Thr Ser
1640                1645                1650

Leu Leu Lys Ile Arg Arg Gly Leu Glu Thr Gly Trp Ala Tyr Thr
1655                1660                1665

His Gln Gly Gly Ile Ser Ser Val Asp His Val Thr Cys Gly Lys
1670                1675                1680

Asp Leu Leu Val Cys Asp Thr Met Gly Arg Thr Arg Val Val Cys
1685                1690                1695

Gln Ser Asn Asn Lys Met Thr Asp Glu Ser Glu Tyr Gly Val Lys
1700                1705                1710

Thr Asp Ser Gly Cys Pro Glu Gly Ala Arg Cys Tyr Val Phe Asn
1715                1720                1725

Pro Glu Ala Val Asn Ile Ser Gly Thr Lys Gly Ala Met Val His
1730                1735                1740

Leu Gln Lys Thr Gly Gly Glu Phe Thr Cys Val Thr Ala Ser Gly
1745                1750                1755

Thr Pro Ala Phe Phe Asp Leu Lys Asn Leu Lys Gly Trp Ser Gly
1760                1765                1770

Leu Pro Ile Phe Glu Ala Ser Ser Gly Arg Val Val Gly Arg Val
1775                1780                1785

Lys Val Gly Lys Asn Glu Asp Ser Lys Pro Thr Lys Leu Met Ser
```

-continued

```
            1790                1795                1800
Gly Ile Gln Thr Val Ser Lys Ser Thr Thr Asp Leu Thr Glu Met
            1805                1810                1815

Val Lys Lys Ile Thr Thr Met Asn Arg Gly Glu Phe Arg Gln Ile
            1820                1825                1830

Thr Leu Ala Thr Gly Ala Gly Lys Thr Thr Glu Leu Pro Arg Ser
            1835                1840                1845

Val Ile Glu Glu Ile Gly Arg His Lys Arg Val Leu Val Leu Ile
            1850                1855                1860

Pro Leu Arg Ala Ala Ala Glu Ser Val Tyr Gln Tyr Met Arg Gln
            1865                1870                1875

Lys His Pro Ser Ile Ala Phe Asn Leu Arg Ile Gly Glu Met Lys
            1880                1885                1890

Glu Gly Asp Met Ala Thr Gly Ile Thr Tyr Ala Ser Tyr Gly Tyr
            1895                1900                1905

Phe Cys Gln Met Pro Gln Pro Lys Leu Arg Ala Ala Met Val Glu
            1910                1915                1920

Tyr Ser Phe Ile Phe Leu Asp Glu Tyr His Cys Ala Thr Pro Glu
            1925                1930                1935

Gln Leu Ala Ile Met Gly Lys Ile His Arg Phe Ser Glu Asn Leu
            1940                1945                1950

Arg Val Val Ala Met Thr Ala Thr Pro Ala Gly Thr Val Thr Thr
            1955                1960                1965

Thr Gly Gln Lys His Pro Ile Glu Glu Tyr Ile Ala Pro Glu Val
            1970                1975                1980

Met Lys Gly Glu Asp Leu Gly Ser Glu Tyr Leu Asp Ile Ala Gly
            1985                1990                1995

Leu Lys Ile Pro Val Glu Glu Met Lys Ser Asn Met Leu Val Phe
            2000                2005                2010

Val Pro Thr Arg Asn Met Ala Val Glu Thr Ala Lys Lys Leu Lys
            2015                2020                2025

Ala Lys Gly Tyr Asn Ser Gly Tyr Tyr Tyr Ser Gly Glu Asp Pro
            2030                2035                2040

Ser Asn Leu Arg Val Val Thr Ser Gln Ser Pro Tyr Val Val Val
            2045                2050                2055

Ala Thr Asn Ala Ile Glu Ser Gly Val Thr Leu Pro Asp Leu Asp
            2060                2065                2070

Val Val Val Asp Thr Gly Leu Lys Cys Glu Lys Arg Ile Arg Leu
            2075                2080                2085

Ser Pro Lys Met Pro Phe Ile Val Thr Gly Leu Lys Arg Met Ala
            2090                2095                2100

Val Thr Ile Gly Glu Gln Ala Gln Arg Arg Gly Arg Val Gly Arg
            2105                2110                2115

Val Lys Pro Gly Arg Tyr Tyr Arg Ser Gln Glu Thr Pro Val Gly
            2120                2125                2130

Ser Lys Asp Tyr His Tyr Asp Leu Leu Gln Ala Gln Arg Tyr Gly
            2135                2140                2145

Ile Glu Asp Gly Ile Asn Ile Thr Lys Ser Phe Arg Glu Met Asn
            2150                2155                2160

Tyr Asp Trp Ser Leu Tyr Glu Glu Asp Ser Leu Met Ile Thr Gln
            2165                2170                2175

Leu Glu Ile Leu Asn Asn Leu Leu Ile Ser Glu Glu Leu Pro Met
            2180                2185                2190
```

```
Ala Val Lys Asn Ile Met Ala Arg Thr Asp His Pro Glu Pro Ile
2195                2200                2205

Gln Leu Ala Tyr Asn Ser Tyr Glu Thr Gln Val Pro Val Leu Phe
2210                2215                2220

Pro Lys Ile Lys Asn Gly Glu Val Thr Asp Ser Tyr Asp Asn Tyr
2225                2230                2235

Thr Phe Leu Asn Ala Arg Lys Leu Gly Asp Asp Val Pro Pro Tyr
2240                2245                2250

Val Tyr Ala Thr Glu Asp Glu Asp Leu Ala Val Glu Leu Leu Gly
2255                2260                2265

Leu Asp Trp Pro Asp Pro Gly Asn Gln Gly Thr Val Glu Ala Gly
2270                2275                2280

Arg Ala Leu Lys Gln Val Val Gly Leu Ser Thr Ala Glu Asn Ala
2285                2290                2295

Leu Leu Val Ala Leu Phe Gly Tyr Val Gly Tyr Gln Ala Leu Ser
2300                2305                2310

Lys Arg His Ile Pro Val Val Thr Asp Ile Tyr Ser Ile Glu Asp
2315                2320                2325

His Arg Leu Glu Asp Thr Thr His Leu Gln Tyr Ala Pro Asn Ala
2330                2335                2340

Ile Lys Thr Glu Gly Lys Glu Thr Glu Leu Lys Glu Leu Ala Gln
2345                2350                2355

Gly Asp Val Gln Arg Cys Met Glu Ala Met Thr Asn Tyr Ala Arg
2360                2365                2370

Asp Gly Ile Gln Phe Met Lys Ser Gln Ala Leu Lys Val Lys Glu
2375                2380                2385

Thr Pro Thr Tyr Lys Glu Thr Met Asp Thr Val Ala Asp Tyr Val
2390                2395                2400

Lys Lys Phe Met Glu Ala Leu Ala Asp Ser Lys Glu Asp Ile Ile
2405                2410                2415

Lys Tyr Gly Leu Trp Gly Thr His Thr Thr Leu Tyr Lys Ser Ile
2420                2425                2430

Gly Ala Arg Leu Gly Asn Glu Thr Ala Phe Ala Thr Leu Val Val
2435                2440                2445

Lys Trp Leu Ala Phe Gly Gly Glu Ser Ile Ala Asp His Val Lys
2450                2455                2460

Gln Ala Ala Thr Asp Leu Val Val Tyr Tyr Ile Ile Asn Arg Pro
2465                2470                2475

Gln Phe Pro Gly Asp Thr Glu Thr Gln Gln Glu Gly Arg Lys Phe
2480                2485                2490

Val Ala Ser Leu Leu Val Ser Ala Leu Ala Thr Tyr Thr Tyr Lys
2495                2500                2505

Ser Trp Asn Tyr Asn Asn Leu Ser Lys Ile Val Glu Pro Ala Leu
2510                2515                2520

Ala Thr Leu Pro Tyr Ala Ala Thr Ala Leu Lys Leu Phe Ala Pro
2525                2530                2535

Thr Arg Leu Glu Ser Val Val Ile Leu Ser Thr Ala Ile Tyr Lys
2540                2545                2550

Thr Tyr Leu Ser Ile Arg Arg Gly Lys Ser Asp Gly Leu Leu Gly
2555                2560                2565

Thr Gly Val Ser Ala Ala Met Glu Ile Met Ser Gln Asn Pro Val
2570                2575                2580
```

| | | | | | | | | | | | |
|---|---|---|---|---|---|---|---|---|---|---|---|
|Ser|Val|Gly|Ile|Ala|Val|Met|Leu|Gly|Val|Gly|Ala|Val|Ala|Ala|
|2585| | | | |2590| | | |2595| | | | | |

Ser Val Gly Ile Ala Val Met Leu Gly Val Gly Ala Val Ala Ala
2585                2590              2595

His Asn Ala Ile Glu Ala Ser Glu Gln Lys Arg Thr Leu Leu Met
2600                2605              2610

Lys Val Phe Val Lys Asn Phe Leu Asp Gln Ala Ala Thr Asp Glu
2615                2620              2625

Leu Val Lys Glu Ser Pro Glu Lys Ile Ile Met Ala Leu Phe Glu
2630                2635              2640

Ala Val Gln Thr Val Gly Asn Pro Leu Arg Leu Val Tyr His Leu
2645                2650              2655

Tyr Gly Val Phe Tyr Lys Gly Trp Glu Ala Lys Glu Leu Ala Gln
2660                2665              2670

Arg Thr Ala Gly Arg Asn Leu Phe Thr Leu Ile Met Phe Glu Ala
2675                2680              2685

Val Glu Leu Leu Gly Val Asp Ser Glu Gly Lys Ile Arg Gln Leu
2690                2695              2700

Ser Ser Asn Tyr Ile Leu Glu Leu Leu Tyr Lys Phe Arg Asp Ser
2705                2710              2715

Ile Lys Ser Ser Val Arg Gln Met Ala Ile Ser Trp Ala Pro Ala
2720                2725              2730

Pro Phe Ser Cys Asp Trp Thr Pro Thr Asp Arg Ile Gly Leu
2735                2740              2745

Pro Gln Asp Asn Phe Leu Arg Val Glu Thr Lys Cys Pro Cys Gly
2750                2755              2760

Tyr Lys Met Lys Ala Val Lys Asn Cys Ala Gly Glu Leu Arg Leu
2765                2770              2775

Leu Glu Glu Glu Gly Ser Phe Leu Cys Arg Asn Lys Phe Gly Arg
2780                2785              2790

Gly Ser Arg Asn Tyr Arg Val Thr Lys Tyr Tyr Asp Asp Asn Leu
2795                2800              2805

Ser Glu Ile Lys Pro Val Ile Arg Met Glu Gly His Val Glu Leu
2810                2815              2820

Tyr Tyr Lys Gly Ala Thr Ile Lys Leu Asp Phe Asn Asn Ser Lys
2825                2830              2835

Thr Ile Leu Ala Thr Asp Lys Trp Glu Val Asp His Ser Thr Leu
2840                2845              2850

Val Arg Val Leu Lys Arg His Thr Gly Ala Gly Tyr Arg Gly Ala
2855                2860              2865

Tyr Leu Gly Glu Lys Pro Asn His Lys His Leu Ile Glu Arg Asp
2870                2875              2880

Cys Ala Thr Ile Thr Lys Asp Lys Val Cys Phe Leu Lys Met Lys
2885                2890              2895

Arg Gly Cys Ala Phe Thr Tyr Asp Leu Ser Leu His Asn Leu Thr
2900                2905              2910

Arg Leu Ile Glu Leu Val His Lys Asn Asn Leu Glu Asp Lys Glu
2915                2920              2925

Ile Pro Ala Val Thr Val Thr Trp Leu Ala Tyr Thr Phe Val
2930                2935              2940

Asn Glu Asp Ile Gly Thr Ile Lys Pro Ala Phe Gly Glu Lys Ile
2945                2950              2955

Thr Pro Glu Met Gln Glu Glu Ile Thr Leu Gln Pro Ala Val Val
2960                2965              2970

Val Asp Ala Thr Asp Val Thr Val Thr Val Val Gly Glu Thr Pro

```
            2975                2980                2985

Thr Met Thr Thr Gly Glu Thr Pro Thr Thr Phe Thr Ser Ser Gly
    2990                2995                3000

Pro Asp Pro Lys Gly Gln Gln Val Leu Lys Leu Gly Val Gly Glu
    3005                3010                3015

Gly Gln Tyr Pro Gly Thr Asn Pro Gln Arg Ala Ser Leu His Glu
    3020                3025                3030

Ala Ile Gln Ser Ala Asp Glu Arg Pro Ser Val Leu Ile Leu Gly
    3035                3040                3045

Ser Asp Lys Ala Thr Ser Asn Arg Val Lys Thr Val Lys Asn Val
    3050                3055                3060

Lys Val Tyr Arg Gly Arg Asp Pro Leu Glu Val Arg Asp Met Met
    3065                3070                3075

Arg Arg Gly Lys Ile Leu Val Ile Ala Leu Ser Arg Val Asp Asn
    3080                3085                3090

Ala Leu Leu Lys Phe Val Asp Tyr Lys Gly Thr Phe Leu Thr Arg
    3095                3100                3105

Glu Thr Leu Glu Ala Leu Ser Leu Gly Arg Pro Lys Lys Lys Asn
    3110                3115                3120

Ile Thr Lys Ala Glu Ala Gln Trp Leu Leu Arg Leu Glu Asp Gln
    3125                3130                3135

Met Glu Glu Leu Pro Asp Trp Phe Ala Ala Gly Glu Pro Ile Phe
    3140                3145                3150

Leu Glu Ala Asn Ile Lys His Asp Arg Tyr His Leu Val Gly Asp
    3155                3160                3165

Ile Ala Thr Ile Lys Glu Lys Ala Lys Gln Leu Gly Ala Thr Asp
    3170                3175                3180

Ser Thr Lys Ile Ser Lys Glu Val Gly Ala Lys Val Tyr Ser Met
    3185                3190                3195

Lys Leu Ser Asn Trp Val Met Gln Glu Glu Asn Lys Gln Ser Asn
    3200                3205                3210

Leu Thr Pro Leu Phe Glu Glu Leu Leu Gln Gln Cys Pro Pro Gly
    3215                3220                3225

Gly Gln Asn Lys Thr Ala His Met Val Ser Ala Tyr Gln Leu Ala
    3230                3235                3240

Gln Gly Asn Trp Met Pro Thr Ser Cys His Val Phe Met Gly Thr
    3245                3250                3255

Ile Ser Ala Arg Arg Thr Lys Thr His Pro Tyr Glu Ala Tyr Val
    3260                3265                3270

Lys Leu Arg Glu Leu Val Glu Glu His Lys Met Lys Thr Leu Cys
    3275                3280                3285

Pro Gly Ser Ser Leu Arg Lys His Asn Glu Trp Val Ile Gly Lys
    3290                3295                3300

Ile Lys Tyr Gln Gly Asn Leu Arg Thr Lys His Met Leu Asn Pro
    3305                3310                3315

Gly Lys Val Ala Glu Gln Leu His Arg Glu Gly His Arg His Asn
    3320                3325                3330

Val Tyr Asn Lys Thr Ile Gly Ser Val Met Thr Ala Thr Gly Ile
    3335                3340                3345

Arg Leu Glu Lys Leu Pro Val Val Arg Ala Gln Thr Asp Thr Thr
    3350                3355                3360

Asn Phe His Gln Ala Ile Arg Asp Lys Ile Asp Lys Glu Glu Asn
    3365                3370                3375
```

-continued

```
Leu Gln Thr Pro Gly Leu His Lys Lys Leu Met Glu Val Phe Asn
    3380                3385                3390

Ala Leu Lys Arg Pro Glu Leu Glu Ser Ser Tyr Asp Ala Val Glu
    3395                3400                3405

Trp Glu Glu Leu Glu Arg Gly Ile Asn Arg Lys Gly Ala Ala Gly
    3410                3415                3420

Phe Phe Glu Arg Lys Asn Ile Gly Glu Ile Leu Asp Ser Glu Lys
    3425                3430                3435

Asn Lys Val Glu Glu Ile Ile Asp Asn Leu Lys Lys Gly Arg Asn
    3440                3445                3450

Ile Lys Tyr Tyr Glu Thr Ala Ile Pro Lys Asn Glu Lys Arg Asp
    3455                3460                3465

Val Asn Asp Asp Trp Thr Ala Gly Asp Phe Val Asp Glu Lys Lys
    3470                3475                3480

Pro Arg Val Ile Gln Tyr Pro Glu Ala Lys Thr Arg Leu Ala Ile
    3485                3490                3495

Thr Lys Val Met Tyr Lys Trp Val Lys Gln Lys Pro Val Val Ile
    3500                3505                3510

Pro Gly Tyr Glu Gly Lys Thr Pro Leu Phe Gln Ile Phe Asp Lys
    3515                3520                3525

Val Lys Lys Glu Trp Asp Gln Phe Gln Asn Pro Val Ala Val Ser
    3530                3535                3540

Phe Asp Thr Lys Ala Trp Asp Thr Gln Val Thr Thr Asn Asp Leu
    3545                3550                3555

Glu Leu Ile Lys Asp Ile Gln Lys Tyr Tyr Phe Lys Lys Lys Trp
    3560                3565                3570

His Lys Phe Ile Asp Thr Leu Thr Met His Met Ser Glu Val Pro
    3575                3580                3585

Val Ile Thr Ala Asp Gly Glu Val Tyr Ile Arg Lys Gly Gln Arg
    3590                3595                3600

Gly Ser Gly Gln Pro Asp Thr Ser Ala Gly Asn Ser Met Leu Asn
    3605                3610                3615

Val Leu Thr Met Val Tyr Ala Phe Cys Glu Ala Thr Gly Val Pro
    3620                3625                3630

Tyr Lys Ser Phe Asp Arg Val Ala Lys Ile His Val Cys Gly Asp
    3635                3640                3645

Asp Gly Phe Leu Ile Thr Glu Arg Ala Leu Gly Glu Lys Phe Ala
    3650                3655                3660

Ser Lys Gly Val Gln Ile Leu Tyr Glu Ala Gly Lys Pro Gln Lys
    3665                3670                3675

Ile Thr Glu Gly Asp Lys Met Lys Val Ala Tyr Gln Phe Asp Asp
    3680                3685                3690

Ile Glu Phe Cys Ser His Thr Pro Ile Gln Val Arg Trp Ser Asp
    3695                3700                3705

Asn Thr Ser Ser Tyr Met Pro Gly Arg Asn Thr Thr Thr Ile Leu
    3710                3715                3720

Ala Lys Met Ala Thr Arg Leu Asp Ser Ser Gly Glu Arg Gly Thr
    3725                3730                3735

Ile Ala Tyr Glu Lys Ala Val Ala Phe Ser Phe Leu Leu Met Tyr
    3740                3745                3750

Ser Trp Asn Pro Leu Ile Arg Arg Ile Cys Leu Leu Val Leu Ser
    3755                3760                3765
```

```
Thr Glu Leu Gln Val Lys Pro Gly Lys Ser Thr Thr Tyr Tyr Tyr
    3770            3775            3780

Glu Gly Asp Pro Ile Ser Ala Tyr Lys Glu Val Ile Gly His Asn
    3785            3790            3795

Leu Phe Asp Leu Lys Arg Thr Ser Phe Glu Lys Leu Ala Lys Leu
    3800            3805            3810

Asn Leu Ser Met Ser Val Leu Gly Ala Trp Thr Arg His Thr Ser
    3815            3820            3825

Lys Arg Leu Leu Gln Asp Cys Val Asn Met Gly Val Lys Glu Gly
    3830            3835            3840

Asn Trp Leu Val Asn Ala Asp Arg Leu Val Ser Ser Lys Thr Gly
    3845            3850            3855

Asn Arg Tyr Val Pro Gly Glu Gly His Thr Leu Gln Gly Arg His
    3860            3865            3870

Tyr Glu Glu Leu Val Leu Ala Arg Lys Gln Ile Asn Ser Phe Gln
    3875            3880            3885

Gly Thr Asp Arg Tyr Asn Leu Gly Pro Ile Val Asn Met Val Leu
    3890            3895            3900

Arg Arg Leu Arg Val Met Met Met Thr Leu Ile Gly Arg Gly Val
    3905            3910            3915

<210> SEQ ID NO 5
<211> LENGTH: 54
<212> TYPE: DNA
<213> ORGANISM: Classical Swine Fever Virus

<400> SEQUENCE: 5
ccagtgagtt gcacccactt agccgcggcc gactataaag acgatgatga caaa           54

<210> SEQ ID NO 6
<211> LENGTH: 54
<212> TYPE: DNA
<213> ORGANISM: Classical Swine Fever Virus

<400> SEQUENCE: 6
cctgtctctt gtacacatct tgcggccgca gattacaagg atgacgacga taag           54

<210> SEQ ID NO 7
<211> LENGTH: 18
<212> TYPE: PRT
<213> ORGANISM: Classical Swine Fever Virus

<400> SEQUENCE: 7

Pro Val Ser Cys Thr His Leu Ala Ala Ala Asp Tyr Lys Asp Asp
1               5                   10                  15

Asp Lys

<210> SEQ ID NO 8
<211> LENGTH: 58
<212> TYPE: DNA
<213> ORGANISM: Artificial Sequence
<220> FEATURE:
<223> OTHER INFORMATION: Chemically Synthesized

<400> SEQUENCE: 8
gttactggta actggggcac cagtgagttg cacccacctt gcggccgcag attacaag       58

<210> SEQ ID NO 9
<211> LENGTH: 58
<212> TYPE: DNA
```

```
<213> ORGANISM: Artificial Sequence
<220> FEATURE:
<223> OTHER INFORMATION: Chemically Synthesized

<400> SEQUENCE: 9
cttgtaatct gcggccgcaa ggtgggtgca actcactggt gccccagtta ccagtaac       58

<210> SEQ ID NO 10
<211> LENGTH: 58
<212> TYPE: DNA
<213> ORGANISM: Artificial Sequence
<220> FEATURE:
<223> OTHER INFORMATION: Chemically Synthesized

<400> SEQUENCE: 10
caccagtgag ttgcacccac ttagccgcgg ccgactataa ggatgacgac gataagca       58

<210> SEQ ID NO 11
<211> LENGTH: 58
<212> TYPE: DNA
<213> ORGANISM: Artificial Sequence
<220> FEATURE:
<223> OTHER INFORMATION: Chemically Synthesized

<400> SEQUENCE: 11
tgcttatcgt cgtcatcctt atagtcggcc gcggctaagt gggtgcaact cactggtg       58

<210> SEQ ID NO 12
<211> LENGTH: 55
<212> TYPE: DNA
<213> ORGANISM: Artificial Sequence
<220> FEATURE:
<223> OTHER INFORMATION: Chemically Synthesized

<400> SEQUENCE: 12
cccacttagc cgcggccgac tataaagacg atgatgacaa acaaggccgg ctagc          55

<210> SEQ ID NO 13
<211> LENGTH: 55
<212> TYPE: DNA
<213> ORGANISM: Artificial Sequence
<220> FEATURE:
<223> OTHER INFORMATION: Chemically Synthesized

<400> SEQUENCE: 13
gctagccggc cttgtttgtc atcatcgtct ttatagtcgg ccgcggctaa gtggg          55

<210> SEQ ID NO 14
<211> LENGTH: 15
<212> TYPE: DNA
<213> ORGANISM: Classical Swine Fever Virus

<400> SEQUENCE: 14
tcatttaata tggac                                                      15

<210> SEQ ID NO 15
<211> LENGTH: 5
<212> TYPE: PRT
<213> ORGANISM: Classical Swine Fever Virus

<400> SEQUENCE: 15

Ser Phe Asn Met Asp
1               5

<210> SEQ ID NO 16
```

```
<211> LENGTH: 15
<212> TYPE: DNA
<213> ORGANISM: Classical Swine Fever Virus

<400> SEQUENCE: 16
agtttcggaa tggat                                                          15

<210> SEQ ID NO 17
<211> LENGTH: 5
<212> TYPE: PRT
<213> ORGANISM: Classical Swine Fever Virus

<400> SEQUENCE: 17

Ser Phe Gly Met Asp
1               5

<210> SEQ ID NO 18
<211> LENGTH: 46
<212> TYPE: DNA
<213> ORGANISM: Artificial Sequence
<220> FEATURE:
<223> OTHER INFORMATION: Chemically Synthesized

<400> SEQUENCE: 18
gacgggtgtt atagagtgca cgagtttcgg aatggatact ctgaga                        46

<210> SEQ ID NO 19
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 19
tctcagagta tccttccgaa acttgacgtg cactctataa cacccgtc                      48
```

LIVE ATTENUATED ANTIGENICALLY MARKED CLASSICAL SWINE FEVER VACCINE

BACKGROUND OF THE INVENTION

1. Field of the Invention

This invention relates to the design of a double antigenically marked classical swine fever virus (CSFV) live attenuated candidate strain vaccine validated for absence of reversions. The FlagT4-mFT-Gv virus is a modified recombinant FlagT4 RB-C22 virus containing a multiple-mutated Flag insertion epitope in the E1 glycoprotein and a multiple-mutated WH303 epitope in the E2 glycoprotein.

2. Description of the Relevant Art

Classical swine fever (CSF) is a highly contagious disease of swine. The etiological agent, CSF virus (CSFV), is a small, enveloped virus with a positive, single-stranded RNA genome, classified as a member of the genus Pestivirus within the family Flaviridae (Becher et al. 2003. *Virology* 311: 96-104). The 12.5 kb CSFV genome contains a single open reading frame that encodes a 3898-amino-acid polyprotein and ultimately yields 11 to 12 final cleavage products ($NH_2$-Npro-C-$E^{rns}$-E1-E2-p7-N52-N53-NS4A-NS4B-NS5A-NS5B-COOH) through co- and post-translational processing of the polyprotein by cellular and viral proteases (Rice, C. M. 1996. In: *Fundamental Virology*, 3rd edition, Fields and Howley, eds., Lippincott Raven, Philadelphia, pp. 931-959). Structural components of the CSFV virion include the capsid (C) protein and glycoproteins $E^{rns}$, E1, and E2. The E1 and E2 glycoproteins are anchored to the envelope at their carboxyl termini and $E^{rns}$ loosely associates with the viral envelope (Thiel et al. 1991. *J. Virol.* 65: 4705-4712; Weiland et al. 1990. *J. Virol.* 64: 3563-3569; Weiland et al. 1999. *J. Gen. Virol.* 80: 1157-1165). E1 and E2 are type I transmembrane proteins with an N-terminal ectodomain and a C-terminal hydrophobic anchor (Thiel et al., supra). E2 is the most immunogenic of the CSFV glycoproteins (Konig et al. 1995. *J. Virol.* 69: 6479-6486; van Gennip et al. 2000. *Vaccine* 19:447-459); Weiland et al. 1990, supra), inducing neutralizing antibodies, which provide protection against lethal CSFV challenge.

The two main policies used for CSFV control are prophylactic vaccination or non-vaccination with "stamping out" of exposed animals in the event of an outbreak. Countries considered free of CSF do not recommend the use of currently available live attenuated viruses as tools to control outbreaks of the disease, despite the proven efficacy of these vaccines in eliciting a rapid and solid protection against the virus (van Oirschot, J. T. 2003. *Vet. Microbiol.* 96: 367-384). The humoral immune response induced by these vaccines does not differ from that elicited by infections caused by wild-type viruses; hence, the use of CSFV live attenuated viruses has been hampered by their inability of inducing a response differentiable between infected and vaccinated animals, i.e., by their lack of DIVA capability. Thus, the use of a CSFV live attenuated virus with DIVA capabilities could significantly impact policies of disease control. CSFV subunit marker vaccines with DIVA capabilities have been developed using recombinant CSFV E2 envelope protein (Hulst et al. 1993. *J. Virol.* 67: 5435-5442; Van Rijn et al. 1996. *J. Gen. Virol.* 77: 2737-2745; Van Rijn et al. 1999. *Vaccine* 17: 433-440)). The onset of immunity elicited by subunit vaccines occurs two weeks post-vaccination, limiting their efficacy relative to traditional live attenuated virus vaccines when animals are exposed to CSFV shortly after vaccination (Bouma et al. 2000. *Vaccine* 18: 1374-1381; Uttenthal et al. 2001. *Vet. Microbiol.* 83: 85-106).

Recently, we reported the development of a CSFV experimental marker live attenuated virus strain, FlagT4v (Holinka et al. 2009. *Virology* 384:106-113). FlagT4v contains the synthetic epitope of Flag® (Sigma, St. Louis, Mo.) as an insertion within the 19 mer insertion of a previously modified E1. Flag® serves as a positive antigenic marker. FlagT4 also serves as a negative antigenic marker as the result of the abolition of a highly conserved CSFV-specific epitope recognized by monoclonal antibody WH303 (mAbWH303e) (Edwards et al. 1991. *Vet Microbiol.* 29:101-108). Immunization with FlagT4v induced complete protection against challenge with virulent CSFV Brescia, both at 3 and 28 days post-infection (DPI). Serological responses against both the Flag and mAbWH303 epitopes in animals immunized with FlagT4v allowed the discrimination of animals immunized with FlagT4v from animals challenged with CSFV Brescia.

FlagT4 was further analyzed as a candidate vaccine strain and its minimal protective dose, biosafety and attenuation stability were determined. Although FlagT4v was completely atoxic and showed a protective efficacy compatible with further development as a vaccine, it presented some degree of reversion to virulence when successively passed in swine. Thus, there was a need to modify the FlagT4 virus to obtain an attenuated virus that has the attributes of a positive and a negative marker and is also a successful live attenuated vaccine.

SUMMARY OF THE INVENTION

We have developed a novel classical swine fever mutant virus, the FlagT4-mFT-Gv virus.

In accordance with this discovery, it is an object of the invention to provide a recombinant classical swine fever virus (CSFV) mutant virus, the FlagT4-mFT-Gv virus, a modification of the antigenically-marked FlagT4 CSFV. The nucleotide sequence of FlagT4-mFT-Gv (SEQ ID NO:1) differs from the nucleotide sequence encoding the FlagT4 CSFV. While FlagT4-mFT-Gv (SEQ ID NO:1) encodes the same amino acids of the 20 mer Flag-containing insertion of the modified CSFV E1 glycoprotein of FlagT4, all the nucleotide triplets (codons) encoding said amino acids have been changed, if they could be changed because of the redundancy in codons encoding for the same amino acids, and thus differ from the nucleotide sequence (SEQ ID NO:3) encoding the region of the 20 mer Flag-containing insertion of the original FlagT4 live attenuated virus. Further, in the FlagT4-mFT-Gv, an additional change has been made in the T4 region of E2 where both the nucleotide sequence and the amino acid sequence of the T4 region of the modified CSFV E2 glycoprotein of the FlagT4 virus have been further modified. Thus, while the FlagT4-mFT-Gv, like FlagT4, lacks an immunodominant WH303 epitope in the modified T4 region of the E2 glycoprotein, the nucleotide and amino acid sequences of FlagT4 and FlagT4-mFT-Gv differ. The nucleotide sequence of T4 has been changed to encode a T4 region that differs from the T4 region of FlagT4 by one amino acid, namely, asparagine has been changed to glycine; and, further, those nucleotide triplets (codons) encoding the amino acids that remain the same in the T4 region of FlagT4-mFT-Gv and FlagT4 have also been changed where redundant codons for the same amino acids allow.

An added object of the invention is to provide immunogenic compositions comprising a viable recombinant classical swine fever virus mutant, FlagT4-mFT-Gv.

An additional object of the invention is to provide a rationally designed live attenuated CSFV effective to protect an animal from clinical CSF disease when challenged with virulent Brescia CSFV.

A further object of the invention is to provide a marker vaccine which can potentially distinguish between vaccinated animals and animals infected with CSFV.

A still further object of the invention is to provide a vaccine comprising at least one additional vaccine strain capable of inducing protection against CSF or against another porcine pathogen.

Another object of the invention is to provide a method for protecting an animal against CSF by administering an effective amount of rationally designed live attenuated CSFV vaccine.

An additional object of the invention is to provide a method for distinguishing animals infected with CSFV from animals vaccinated with said rationally designed live attenuated CSFV vaccine, comprising: analyzing serum to compare the serological responses to the marker sequences as determined by the ability of said animal serum to recognize the FLAG sequence and WH303 sequence antigens wherein the serologic profile observed for vaccinated animals can be differentiated from the serologic profile observed for wild-type infected animals.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

In FIG. 1A, the nucleotide sequence showing changes in the triplet codons depicts nucleotides 2435-2488 of SEQ ID NO:1 and is identified in the Sequence Listing as SEQ ID NO:5. The nucleotide sequence with no changes in the triplet codons depicts nucleotides 2435-2488 of SEQ ID NO:3, the nucleotide sequence encoding the original FlagT4, and is identified in the Sequence Listing as SEQ ID NO:6. The amino acid sequence depicts amino acids 688 to 705 of SEQ ID NOs: 2 and 4 and is identified in the Sequence Listing as SEQ ID NO:7. Oligonucleotide primers used to introduce nucleotide substitutions are shown. The sequences of the Forward Primers (FP) and Reverse Primers (RP) of Flag 1, Flag 2, and Flag 3 are shown and are identified in the Sequence Listing by SEQ ID NOs: 8, 9, 10, 11, 12, and 13, respectively. FIG. 1B depicts the change of nucleotide sequence tca ttt aat atg gac (SEQ ID NO: 14) encoding SFNMD (SEQ ID NO:15) representing nucleotides 2921-2935 of SEQ ID NO:3 encoding amino acids 849-857 of SEQ ID NO: 4 (FlagT4) to the nucleotide sequence agt ttc gga atg gat (SEQ ID NO:16) encoding SFGMD (SEQ ID NO:17) representing nucleotides 2921-2935 of SEQ ID NO:1 encoding amino acids 849-857 of SEQ ID NO: 2 (FlagT4-mFt-Gv). The sequences of the Forward T4 Primer (FT4) and the Reverse T4 Primer (RT4) are shown and identified as SEQ ID NOs: 18 and 19, respectively.

DETAILED DESCRIPTION OF THE INVENTION

Figure 1A:
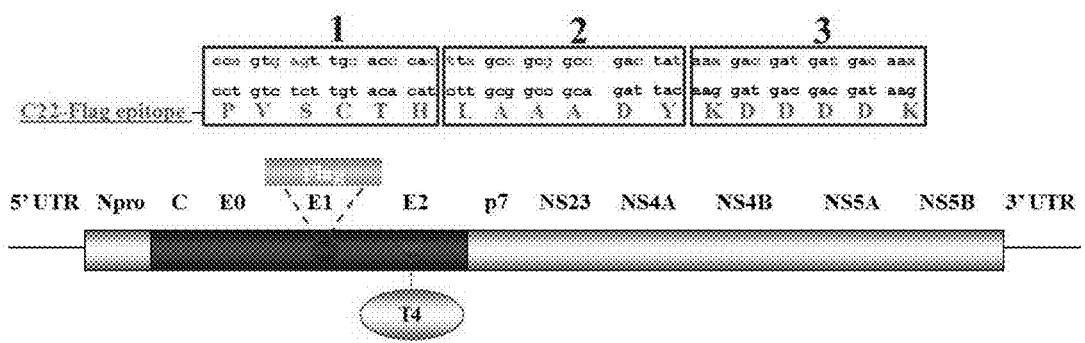
FIGS. 1A and 1B are schematic representations depicting codon changes introduced into the Flag (FIG. 1A) and the T (FIG. 1B) areas of FlagT4-mFT-Gv as compared to the codon usage in the parental FlagT4v.

We have developed a live attenuated CSFV vaccine strain, FlagT4-mFT-Gv (SEQ ID NO:1), a modified version of the FlagT4v where changes in the codon usage were introduced into the genomic areas encoding for Flag and T4 to rectify the reversion of FlagT4 to the virulent genotype. The new virus, FlagT4-mFT-Gv, possesses the same amino acid sequence as FlagT4v except for one substitution, the substitution of asparagine by glycine at position 852 in the T4 region of the CSFV FlagT4 polypeptide. The nucleotide sequence of FlagT4-mFT-Gv (SEQ ID NO:1) differs from the nucleotide sequence encoding the FlagT4 CSFV. The nucleotide sequence of FlagT4-mFT-Gv (SEQ ID NO:1) encodes the same amino acids of the modified CSFV E1 glycoprotein of FlagT4; however, in FlagT4-mFT-Gv, all the nucleotide triplets (codons) of the modified CSFV E1 have been changed, if they could be changed because of the redundancy in codons encoding for the same amino acids, and thus differ from the nucleotide sequence of the original FlagT4 live attenuated virus in the E1 region. Further, in the FlagT4-mFT-Gv, both the nucleotide sequence and the amino acid sequence of the T4 region of the modified CSFV E2 glycoprotein of the FlagT4 virus have been further modified. The region covered by amino acid positions 849-857 of the WH303 epitope of E2 has been changed from TSFNMDTLR to TSFGMDTLR.

The nucleotide sequence (SEQ ID NO:1) of FlagT4-mFT-Gv differs from the nucleotide sequence (SEQ ID NO:3) encoding the FlagT4 CSFV. The nucleotide sequence of FlagT4-mFT-Gv (SEQ ID NO:1) encodes the polypeptide sequence (SEQ ID NO:2). The amino acid sequence of the 20 mer Flag-containing insertion of the modified CSFV E1 glycoprotein of FlagT4-mFT-Gv is the same as the amino acid sequence as is found in the 20 mer Flag-containing insertion of the modified CSFV E1 protein in FlagT4, i.e., amino acids 688-705 representing the Flag region of the E1 glycoprotein of SEQ ID NO:2 (FlagT4-mFT-Gv polypeptide) and amino acids 688-705 representing the E1 portion of SEQ ID NO:4 (FlagT4 polypeptide) are the same. However, all the nucleotide triplets of SEQ ID NO:1 (FlagT4-mFT-Gv) encoding those amino acids of the 20 mer Flag-containing insertion of the modified FlagT4-mFT-Gv E1 protein, i.e., those amino acids identical to the 20 mer Flag-containing insertion of FlagT4, have been changed and differ from the nucleotide triplets of SEQ ID NO:3. Thus, nucleotides 2435-2488 of SEQ ID NO:1 differ from nucleotides 2435-2488 of SEQ ID NO:3, but they encode the same amino acid sequences.

The T4 modification in the E2 glycoprotein of the original FlagT4 resulted in the E2 glycoprotein lacking an immunodominant WH303 epitope. Both the nucleotide sequence and the amino acid sequence of the T4 region of the modified CSFV E2 glycoprotein of FlagT4 have been further modified in the FlagT4-mFT-Gv. In FlagT4-mFT-Gv, the nucleotide sequence of T4 (nucleotide triplet 2927, 2928, 2929 of SEQ ID NO:1) has been changed to encode a T4 region (amino acid 852 of SEQ ID NO:2) that differs from the T4 region of FlagT4 (amino acid 852 of SEQ ID NO:4) by one amino acid, namely, asparagine has been changed to glycine; and, further, those nucleotide triplets (2921-2935 of SEQ ID NO:1) encoding the amino acids that remain the same in the T4 region of FlagT4-mFT-Gv and FlagT4 (amino acids 850, 851, 853 and 854) of SEQ ID NO:2 and SEQ ID NO:4, respectively, have also been changed.

FlagT4-mFT-Gv was shown to efficiently maintain its attenuated phenotype during the reversion to virulence assay. In addition, FlagT4-mFT-Gv was effective in inducing protection to swine against the challenge at 21 days post vaccination with Brescia virulent virus. A serological response against the Flag epitope in FlagT4-mFT-Gv-immunized animals allows the discrimination between a Flag/T4v-immunized and a Brescia-infected animal.

A vaccine is defined herein as a biological agent which is capable of providing a protective response in an animal to which the vaccine has been delivered and is incapable of causing severe disease. Administration of the vaccine results in immunity from a disease; the vaccine stimulates antibody production or cellular immunity against the pathogen causing the disease. Immunity is defined herein as the induction of a significant higher level of protection in a population of swine against mortality and clinical symptoms after vaccination compared to an unvaccinated group. In particular, the vaccine according to the invention protects a large proportion of vaccinated animals against the occurrence of clinical symptoms of the disease and mortality. The vaccine of the invention herein is a genetically engineered mutant virus vaccine. A marker vaccine is defined as a vaccine that, in conjunction with a diagnostic test, enables serological differentiation of vaccinated animals from infected animals. A mutation is understood to be a change in the genetic information of a "wild-type" or unmodified E1 or E2 gene of a parent CSFV strain which is able to express native E1 and E2 proteins. Thus, the E1 and E2 polypeptides expressed by the FlagT4-mFT-Gv mutant virus are changed: the E1 protein displays a Flag epitope within the altered (by insertion) E1 protein and the E2 protein lacks a wild-type immunodominant WH303 epitope. The FlagT4-mFT-Gv recombinant classical swine fever virus (CSFV) mutant comprising DNA encoding a mutation in CSFV E1 glycoprotein, wherein the mutation comprises a 20 mer insertion, wherein said 20 mer insertion comprises the FLAG™ epitope as a positive mutation marker in the mutant CSFV E1, wherein said recombinant CSFV mutant is a live attenuated CSFV and said FLAG™ epitope carried by said live attenuated CSFV is capable of being recognized by monoclonal antibodies specifically binding to said FLAG™ epitope, which serves as a positive marker for said attenuated CSFV mutant and further comprises another mutation in CSFV E2 glycoprotein in addition to said positive mutation marker in CSFV E1 glycoprotein, wherein the mutant CSFV E2 glycoprotein comprises a substitution mutation in the wild-type WH303 immunogenic epitope wherein amino acids are substituted with the epitope of TSFGM-DTLR thus resulting in the elimination of the immunodominant WH303 epitope of the wild-type CSFV and wherein said recombinant CSFV mutant is live attenuated CSFV having both the positive marker as a result of the mutation in CSFV E1 glycoprotein and the negative marker as a result of the mutation in the wild-type WH303 epitope in CSFV E2 glycoprotein.

A vaccine against CSFV is provided that comprises a FlagT4-mFT-Gv virus mutant as defined above in a live form, and a pharmaceutically acceptable carrier or diluent. The vaccine according to the invention containing the live virus can be prepared and marketed in the form of a suspension or in a lyophilized form and additionally contains a pharmaceutically acceptable carrier or diluent customary used for such compositions. Carriers include stabilizers, preservatives and buffers. Suitable stabilizers are, for example SPGA (sucrose, phosphate, glutamate, and human. albumin), carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are well known in the art. Furthermore, nucleic acid sequences encoding polypeptides for pharmaceutical or diagnostic applications, in particular immunomodulators such as lymphokines, interferons or cytokines, may be incorporated into the vaccine.

A vaccine according to the invention can be prepared by conventional methods such as those commonly used for the commercially available live attenuated CSFV vaccines. Briefly, a susceptible substrate is inoculated with the FlagT4-mFT-Gv mutant and propagated until the virus has replicated to a desired titer after which FlagT4-mFT-Gv-containing material is harvested. Subsequently, the harvested material is formulated into a pharmaceutical preparation with immunizing properties.

Every substrate which is able to support the replication of FlagT4-mFT-Gv viruses can be used in the present invention, including Swine kidney cells (SK6) and primary cultures of swine peripheral blood macrophages.

The vaccine may be administered by intramuscular, intradermal, subcutaneous or intranasal inoculation or injection in an amount which is effective to protect the animal against challenge by a virulent strain of CSFV. This amount may vary according to the animal being inoculated, taking into consideration the size and weight of the animal. The vaccine according to the invention comprises an effective dosage of the FlagT4-mFT-Gv mutant as the active component, i.e. an amount of immunizing FlagT4-mFT-Gv material that will induce immunity in the vaccinated animals, swine, against challenge by a virulent CSFV. Immunity is defined herein as the induction of a significant higher level of protection in a population of swine against mortality and clinical symptoms after vaccination compared to an unvaccinated group. In particular, the vaccine according to the invention prevents a large proportion of vaccinated animals against the occurrence of clinical symptoms of the disease and mortality. Typically, the live vaccine can be administered in a dose of $10^4$-$10^5$ TCID$_{50}$. Effective amounts may be experimentally determined as necessary by those of skill in the art by following the guidance provided, for example, by Example 5.

In addition to the FlagT4-mFT-Gv mutant, the invention can also include combination vaccines comprising a vaccine strain capable of inducing protection against another porcine pathogen.

The FlagT4-mFT-Gv marker vaccine described above, in conjunction with a diagnostic method, has the potential of distinguishing between animals that are vaccinated with it and animals that are infected with naturally occurring CSFV strains or vaccinated with conventional CSFV vaccines.

The present invention also provides an invaluable tool to monitor CSFV control measures that may lead to eradication of CSFV if applied in large scale stamping out programs. This tool concerns a method for determining CSFV infection in swine comprising the step of examining a sample of the animal for the presence or absence of antibodies reactive with the immunodominant epitopes FLAG and WH303. The sample of the animal used in this method may be any sample in which CSFV or FlagT4-mFT-Gv antibodies can be detected, e.g. a blood, serum or tissue sample.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent, chemiluminescent, radioactive or dye molecules.

Suitable methods for the detection of WH303 and FLAG in the sample include, for example, the enzyme-linked immunosorbent assay (ELISA), immunofluorescent tests and Western blot analysis.

Porcine anti-CSFV sera raised against the FlagT4-mFT-Gv mutant according to the present invention has the potential of being distinguishable from porcine sera raised against naturally occurring CSFV strains and conventional CSFV vaccine strains. Thus, the FlagT4-mFT-Gv mutant has the potential of being a marker vaccine.

Thus, the particular CSFV mutant, FlagT4-mFT-Gv, according to the present invention has the potential of producing antiserum in pigs wherein the antisera are lacking in antibodies that react with an immunodominant epitope, WH303. Such antiserum would score negative in a direct- or blocking WH303 enzyme-linked immunosorbant assay (ELISA).

In an ELISA to detect porcine anti-FLAG and anti-WH303 epitope porcine antibodies, microtitration plates are coated with FLAG-bearing E1 protein (or a FLAG antigen) or wild type E2 protein bearing the WH303 epitope (or an E2 fragment bearing the WH303 epitope). Next, the wells of the coated plates are filled with porcine serum and serial dilutions are made. After incubation, porcine anti-FLAG or anti-WH303 epitope protein serum antibodies are determined by detecting antibody (monoclonal or polyclonal) with the same specificity as the coated one, but which is labeled (e.g. with biotin). The labeled antibody will occupy the free antigens that have not been occupied by anti-WH303 epitope or anti-FLAG antibodies in the porcine serum. For example, horse radish peroxidase coupled to avidin may be added and the amount of peroxidase is measured by an enzymatic reaction. If no antibodies against FLAG-marked E1 or the E2 WH303 epitope are present in the porcine serum sample then a maximum absorption is obtained. If the serum contains many antibodies against the WH303 epitope then a low absorption is expected. Alternatively, after the incubation with porcine serum, the amount of antibodies present in the serum that bound to the WH303 epitope antigen may be determined directly by using an anti-porcine conjugate followed by the enzymatic reaction.

In a sandwich ELISA the wells of a polystyrene microtitration plate can be coated with a monoclonal antibody directed against the WH303 epitope protein, i.e., mAb WH303. Next, the wells of these coated plates are incubated with antigen. After the antigen is captured, the wells are filled with the porcine serum and serial dilutions are made. Subsequently, the protocol as described above may be followed.

In another diagnostic test (Western blot analysis), the FLAG-marked E1 polypeptide or FLAG fragment or the WH303 epitope-containing material is subjected to SDS-PAGE. Next, the separated proteins are electroblotted onto nitro-cellulose membrane. Thereafter, the membranes can be cut into lanes and the lanes are incubated with the porcine serum. The presence in the sample of antibodies specific for the WH303 epitope or antibodies specific for FLAG can be determined by examining whether antibodies bound to the WH303 epitope or the FLAG antigen, for example by using an anti-porcine conjugate followed by an enzymatic reaction. If antibodies against the WH303 epitope or FLAG are present then a band of the appropriate size is identifiable.

The WH303 epitope-containing polypeptide may be any WH303 epitope-containing protein or fragment comprising material which allows the formation of the WH303 epitope antigen-WH303 mAb complex. Similarly, the FLAG-containing polypeptide may be any FLAG-containing protein or fragment comprising material which allows the formation of the FLAG (antigen)-anti-FLAG (antibody) complex. Preferably, the WH303 epitope antigen and the FLAG antigen comprise the expression product of a conventional recombinant host cell or virus, e.g. such as E. coli expressed or baculovirus expressed protein. In a further embodiment of the present invention, a diagnostic test kit is provided which is suitable for performing the diagnostic test according to the invention as described above.

In particular, a diagnostic test kit is provided which comprises in addition to the components usually present, the WH303 epitope antigen or FLAG antigen (if desired, coated onto a solid phase) as the immunological reagent. Other components usually present in such a test kit include, biotin or horseradish peroxidase conjugated antibodies, enzyme substrate, washing buffer etc.

To determine CSFV (BICv) WH303 antigen or FLAG antigen in a test sample from an animal in the field, WH303 mAb and anti-FLAG mAb are used as the immunological reagent, preferably fixed to a solid phase. The test sample is added, and after an incubation time allowing formation of the antibody-antigen complex, a second labeled antibody may be added to detect the complex.

Typically, the absorbance (OD) cut-off value for the ELISA to differentiate positive from negative samples is set at three standard deviations above the average P/N ratios of negative control samples from pigs (where P=the OD of samples from wells coated with a relevant peptide coupled to a carrier molecule and; N=the OD of samples from wells coated with the carrier molecule). A carrier molecule can be a carrier protein, such as BSA, ovalbumin, KLH, a carbohydrate chain or a synthetic amino acid chain.

In an alternative embodiment of the diagnostic method the presence of specific antibodies in porcine serum is examined by incubating the serum and an appropriate antigen in the presence of a monoclonal antibody that specifically reacts with an epitope located within the E2 region.

The recombinant FlagT4-mFT-Gv mutant according to the invention is obtained after transfection of suitable cells (e.g., SK6 cells) with the synthetic RNA transcript of the FlagT4-mFT-Gv mutant genome by electroporation. Finally the recombinant FlagT4-mFT-Gv mutant is harvested from the supernatant of the transformed cells.

It has also been found that FlagT4-mFT-Gv mutant according to the present invention is able to induce a protective immune response, i.e. animals immunized with a vaccine comprising the FlagT4-mFT-Gv mutant are protected against virulent challenge. Moreover, it has been found that antisera of animals infected with naturally occurring CSFV comprise antibodies directed to the WH303 epitope of BICv. Antisera from animals infected with the FlagT4-mFT-Gv mutant virus according to the present invention can be tested according to the methods described above to determine their reactivity with the Flag and WH303 epitope. In addition, it has been found that the FlagT4-mFT-Gv mutant virus as described above is attenuated if compared with the parent BICv virus which is able to produce the native E1 and E2 proteins.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (Terpstra et al. 1990. *Dtsch. Tierarztl. Wochenschr.* 97: 77-79), free of BVDV, were cultured in Dulbecco' minimal essential medium (DMEM) (Gibco, Grand Island, N.Y.) with 10% fetal calf serum (FCS) (Atlas Biologicals, Fort Collins, Colo.). CSFV derived from full-length cDNA copies, including CSFV Brescia strain (BICv) (Risatti et al. 2005a. *J. Virol.* 79: 3787-3796), RB-C22v (Risatti et al. 2005b. *Virology* 343: 116-127), T4v (Risatti et al. 2006. *Virology* 355: 94-101), and FlagT4v (Holinka et al., supra) were propagated in SK6 cells. Titration of CSFV from clinical samples was performed using SK6 cells in 96 well plates (Costar, Cambridge, Mass.). Viral infectivity was detected, after 4 days in culture, by immunoperoxidase assay using the CSFV monoclonal antibody (mAb) WH174 (kindly provided by Georgina Ibata, Veterinary Laboratory Agency, UK) or mAb WH303 (Edwards et al., supra), and the Vectastain ABC kit (Vector Laboratories, Buringames, Calif.). MAb WH174 recognizes and binds to the E2 protein of CSFV at an epitope different from that recognized by mAb WH303. Titers were calculated using the method of Reed and Muench (1938. *Amer. J. Hygiene* 27: 493-497) and expressed as $TCID_{50}$/ml. As performed, test sensitivity was >1.8 $TCID_{50}$/ml.

Example 2

DNA Sequencing and Analysis

Full-length infectious clones and in vitro rescued viruses were completely sequenced with CSFV-specific primers by the dideoxynucleotide chain-termination method (Sanger et al. 1977. *Proc. Natl. Acad. Sci. USA* 74: 5463-5467). Sequencing reactions were prepared with the Dye Terminator Cycle Sequencing Kit (Applied Biosystems, Foster City, Calif.). Reaction products were sequenced on a PRISM 3730xl automated DNA Sequencer (Applied Biosystems). Sequence data were assembled with the Phrap software program (Retrieved from the Internet: phrap.org), with confirmatory assemblies performed using CAP3 (Huang and Madan. 1999. *Genome Res.* 9: 868-877). The final DNA consensus sequence represented, on average, five-fold redundancy at each base position. Sequence comparisons were conducted using BioEdit software (Retrieved from the Internet: mbio.ncsu.edu/BioEdit/bioedit.html).

Example 3

Development of FlagT4-mFT-Gv

Figure 1B:
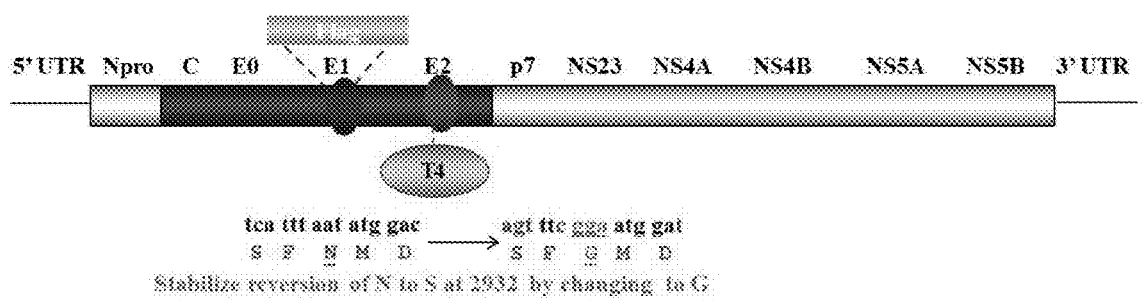

Infectious clone (IC) encoding for the FlagT4-mFT-Gv was designed and developed by modification of the FlagT4v infectious clone. Basically, the Flag area, i.e., the Flag/modified 20 mer insertion of FlagT4v infectious clone, was modified in three different progressive steps (Blocks 1, 2, 3 of FIG. 1A) by site-directed mutagenesis using the primers depicted in FIG. 1A. The site-directed mutagenesis resulted in the new mutant virus FlagT4-mFT-Gv having the identical amino acid sequence as the parent FlagT4v infectious clone virus; however, the codons used to encode the identical amino acids of the mutant virus FlagT4-mFT-Gv were changed (mutated) as compared to the parental virus (FlagT4) as shown in FIG. 1A. Similarly, changes in codon usage were also introduced in the T4 area by a single site-directed mutagenesis step as shown in FIG. 1B. In addition, an amino acid substitution was also included, that is, Asparagine was replaced by Glycine, at position 852 of the CSFV polypeptide (FIG. 1B). Thus, the original FlagT4 peptide SFNMD was replaced by SFGMD where the amino acid asparagine (N) was replaced by glycine (G) and while the remaining amino acids are the same as those of the FlagT4 parent, the codons encoding three of the four remaining (unchanged) amino acids have been changed by site-directed mutagenesis. Altogether, in the new FlagT4-mFT-Gv, one amino acid and 28 nucleotides have been changed.

Infectious RNA was in vitro transcribed from full-length infectious clones of the FlagT4-mFT-Gv and used to transfect SK6 cells as described earlier (Risatti et al., 2005a). Viruses were rescued from transfected cells by day 4 post-transfection. Full-length nucleotide sequences of the rescued virus genomes were identical to parental DNA plasmids, confirming that only predicted mutations were reflected in rescued viruses.

Stability of the attenuated phenotype of FlagT4-mFT-Gv was assessed by the reversion to virulence protocol. Basically, the protocol follows OIE regulations with minor modifications. In brief, a group of five animals (5-6 week old commercial female pigs) were inoculated intramuscularly (IM) with $10^5$ of FlagT4-mFT-Gv. Animals were kept under observation for 7 days and clinical signs and body temperature were recorded. At day $7^{th}$ pi, animals were euthanized and their palatine tonsils removed. Presence of virus was detected in tonsils by virus isolation and by immunohistochemistry using mAb anti-Flag (Sigma) for virus detection. Tonsils were then macerated in a 10% w/v suspension and a pool of tonsil tissue suspension was used to inoculate a new group of 5 animals. This procedure was repeated 5 times until no virus was detected in tonsils of at least one of the five animals evaluated.

There was no presence of CSF-related symptoms in any of the animals in any of the groups. Virus was isolated from tonsils macerates only after the first passage at very low titer ($2.8 \times 10^5$ $TCID_{50}$). These results indicate that FlagT4-mFT-Gv was stably attenuated in swine.

Example 4

Antigenic Profile of FlagT4-mFT-Gv

Infectious RNA was in vitro transcribed from full-length infectious clones of the FlagT4-mFT-Gv and used to transfect SK6 cells as described earlier (Risatti et al. 2005a, supra). Viruses were rescued from transfected cells by day 4 post-transfection.

Figure 2:
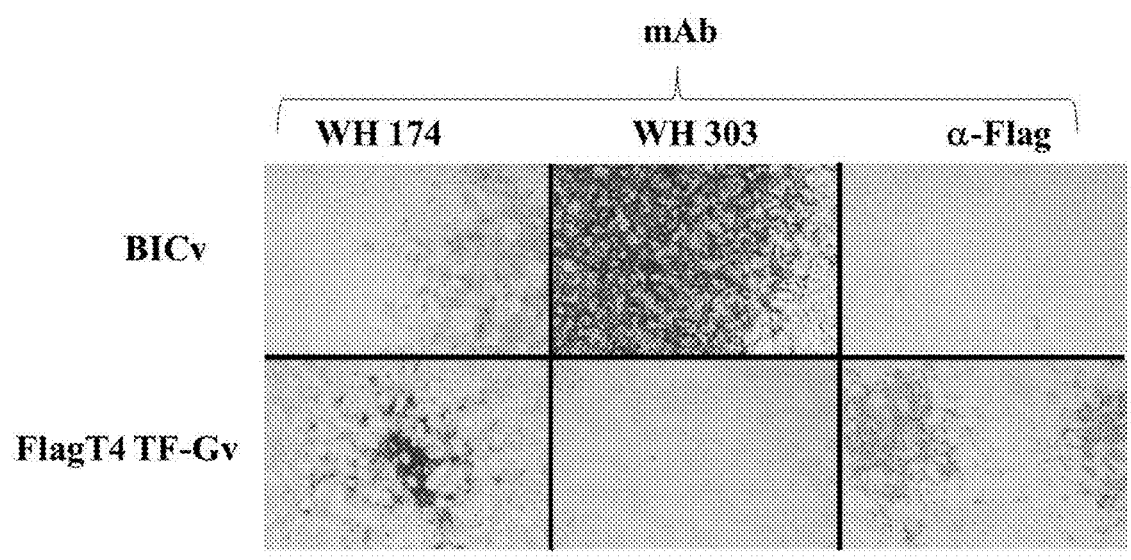
FIG. 2 shows the antigenic profile of FlagT4-mFt-Gv. Sk6 cell cultures were infected with FlagT4-mFt-Gv and 4 days later fixed and stained by immunohistochemistry with mAbs WH303, anti-Flag or WH174.

SK6 cell cultures were infected with FlagT4-mFT-Gv and 4 days later fixed and stained by immunohistochemistry with mAbs WH303, anti-Flag or WH174 in order to analyze its antigenic phenotype. FlagT4-mFT-Gv strongly reacts with mAbs anti-Flag and WH174 and completely fails to react with mAb WH303. Conversely, BICv reacts with mAbs WH303 and WH174, but failed to react with mAb anti-Flag (FIG. 2).

Example 5

Animal Studies

For protection studies, female commercial pigs (40-50 lbs) were allocated in two groups harboring 5 animals each and immunized intramuscularly (IM) with one ml containing $10^5$ TCID$_{50}$ of FlagT4-mFT-Gv or mock vaccinated. At 21 days post immunization (pi), animals were intranasally (IN) challenged with $10^5$ TCID$_{50}$ BICv. Clinical signs and body temperature were recorded daily throughout the experiment as previously described (Risatti et al., 2005b). Blood, serum, and nasal swabs were collected at 7, 14 and 21 days pi and 4, 7, 11, 15, and 21 days post-challenge, with blood obtained from the anterior vena cava in EDTA-containing tubes (Vacutainer) for total and differential white blood cell counts. Total and differential white blood cell and platelet counts were obtained using a Beckman Coulter ACT (Beckman Fullerton, Coulter, Calif.). Tissue samples of palatine tonsil were collected from animals at death or during postmortem examination at 21 days pc and processed as described before (Risatti et al. 2005b, supra) to detect the presence of both FlagT4v and BICv.

The ability of FlagT4-mFT-Gv to induce protection against virulent BICv was assessed in late vaccination-exposure experiments. Groups of pigs (n=6) were IM-inoculated with FlagT4-mFT-Gv and challenged at 21 DPI. Mock-vaccinated control pigs receiving BICv only (n=6) developed anorexia, depression, and fever by 4 days post-challenge (DPC), a marked reduction of circulating leukocytes and platelets by 4 DPC (data not shown), and died or were euthanized in extremis by 6-9 DPC. Pigs challenged at 21 days post-FlagT4-mFT-Gv infection were protected, remaining clinically normal, with no alterations of hematological profiles (data not shown) or presence of fever (Table 1).

These results indicate that protection induced by FlagT4-mFT-Gv was complete, preventing both the presentation of CSF-related clinical signs and the replication of the challenge virus.

As a summary, we present here an approach for rationally developing of an experimental live attenuated marker CSFV vaccine strain, FlagT4-mFT-Gv, which is a derivative of the previous developed FlagT4v. Both FlagT4v and FlagT4-mFT-Gv harbor functional positive and negative antigenic markers that confer potential DIVA capabilities. The virus elicits solid protection against challenge with highly virulent BICv (Brescia strain) by 21 DPI when administered intramuscularly in swine. Potentially, response to FlagT4-mFT-Gv can be distinguished from a wild-type CSF virus (i.e., Brescia strain) by means of serology.

Attenuation of the parental FlagT4v was achieved by manipulating two independent novel genetic determinants of viral virulence (Risatti et al., 2005b; 2006) (i) an insertion of 21 codons in the genomic area encoding for structural glycoprotein E1 and (ii) a change in 5 codons encoding for a the stretch of amino residues in structural glycoprotein E2. FlagT4-mFT-Gv encodes the same amino acids in E1 as are found in FlagT4 E1 but a change in the nucleotide codon produces a substitution of Asparagine by Glycine at position 852. The nucleotide codons encoding E1 and E2 have been changed; thus, the nucleotide sequence of FlagT4-mFT-Gv differs from FlagT4 in the insertion of E1 and the T4 region of E2. SEQ ID NO:1 differs from SEQ ID NO:3. Results presented here demonstrated that these genomic changes pro-

TABLE 1

Survival and fever response in FlagT4-mFT-Gv-vaccinated animals following challenge with BICv.

| Group Vaccinated with | No. of Survivors/ Total | Mean time to Death (Days ± SD) | Fever Days to Onset (Days ± SD) | Duration (Days ± SD) | Maximum Daily Temp (±SD) |
|---|---|---|---|---|---|
| Mock | 0/6 | 7.5 (1.5) | 4.5 (0.57) | 4.5 (1.72) | 105.6 (.32) |
| FlagT4-mFT-Gv | 6/6 | — | — | — | 102.4 (.24) |

Viremia of vaccinated and challenged exposed animals was examined at different times post challenge (Table 2). Detection was performed using mAb WH303, which reacts specifically with the challenge virus BICv. As expected, in mock-vaccinated control animals, viremia was observed within 4 days after challenge, with virus titers remaining high by 7 DPC, the last time point tested before animals died or were euthanized. Conversely, animals inoculated with FlagT4-mFT-Gv and challenged with BICv at 21 DPI did not present viremia (Table 2).

TABLE 2

Viremia in FlagT4-mFT-Gv-infected animals after challenge with virulent BICv.

| Group Vaccinated With | Viremia Duration (Days ± SD) | Maximum (±SD) |
|---|---|---|
| Mock | 7.75 (0.95) | 7.1 (0.25) |
| FlagT4-mFT-Gv | 0 | Neg | duce a stabilization of the attenuated phenotype in FlagT4-mFT-Gv in comparison with the unstable one of the parental FlagT4v.

As a summary, results presented here demonstrated that genetic changes introduced in FlagT4-mFT-Gv produce a stabilization of its attenuated phenotype and that FlagT4-mFT-Gv induce a solid protection against the challenge in animals vaccinated 21 days earlier.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant classical swine fever virus (CSFV) mutant, FlagT4-mFT-Gv, comprising a cDNA sequence as set forth by SEQ ID NO: 1, wherein said recombinant CSFV mutant, FlagT4-mFT-Gv is a live attenuated CSFV capable of being recognized by monoclonal antibodies specifically binding to the FLAG™ epitope, which serves as a positive marker for said attenuated CSFV mutant, wherein said epitope is the eight amino acid peptide DYKDDDDK as set forth in positions 688-705 of SEQ ID NO: 2 and the nucleotide positions 2435-2488 Of SEQ ID NO: 1.

2. The recombinant CSFV mutant of claim 1 further comprising another mutation in CSFV E2 glycoprotein in addition to said positive mutation marker in CSFV E1 glycoprotein, wherein the mutant CSFV E2 glycoprotein of FlagT4-mFT-Gv comprises a substitution mutation in the wild-type WH303 immunogenic epitope, wherein the FlagT4-mFT-Gv substitution is TSFGMDTLR as set forth in positions 849-857 of SEQ ID NO: 2 thereby eliminating the immunodominant WH303 epitope of the wild-type CSFV, wherein said recombinant CSFV mutant is a live attenuated CSFV having both the positive marker as a result of the mutation in CSFV E1 glycoprotein of claim 1 and the negative marker as a result of the mutation in the wild-type WH303 epitope in CSFV E2 glycoprotein.

3. The recombinant CSFV mutant of claim 2 comprising a cDNA sequence as set forth by SEQ ID NO: 1.

4. The recombinant CSFV mutant according to claim 1 wherein the CSFV mutant comprises additional attenuating mutations.

5. A vaccine composition comprising the recombinant CSFV mutant according to any one of claims 1, 2, 3 and 4.

6. An isolated cell infected with the CSFV mutant of any one of claims 1, 2, 3 and 4.

7. A method for the protection of swine against CSF, comprising administering to swine a live attenuated CSF vaccine comprising a recombinant CSFV mutant according to claim 1 in an amount effective to protect said swine from clinical CSF.

8. A method of distinguishing animals naturally infected with CSFV from animals that have been vaccinated with a live attenuated CSF vaccine comprising the recombinant CSFV mutant according to claim 1, comprising: analyzing serum from an animal under evaluation to determine if said serum binds specifically to the FLAG™ epitope.

9. A method for the protection of swine against CSF, comprising administering to swine a live attenuated CSF vaccine comprising a recombinant CSFV mutant according to any one of claims 2 and 3 in an amount effective to protect said swine from clinical CSF.

10. A method of distinguishing animals naturally infected with CSFV from animals that have been vaccinated with a live attenuated CSF vaccine comprising the recombinant CSFV mutant according to any one of claims 1-3, comprising: analyzing serum from an animal under evaluation to determine if the positive marker, the FLAG™ epitope, is present and if the negative marker, the WH303 epitope, is absent.

* * * * *